(12) United States Patent
Ranucci et al.

(10) Patent No.: US 11,234,693 B2
(45) Date of Patent: Feb. 1, 2022

(54) HANDLING OF FASTENERS WITHIN A SURGICAL INSTRUMENT

(71) Applicant: C.R. Bard, Inc., Murray Hill, NJ (US)

(72) Inventors: Kevin J. Ranucci, Warwick, RI (US); Nathan Stewart Cauldwell, Hope, RI (US); Augustus Felix, Cranston, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 532 days.

(21) Appl. No.: 16/268,596

(22) Filed: Feb. 6, 2019

(65) Prior Publication Data

US 2019/0167261 A1 Jun. 6, 2019

Related U.S. Application Data

(63) Continuation of application No. 15/241,904, filed on Aug. 19, 2016, now Pat. No. 10,251,642, which is a
(Continued)

(51) Int. Cl.
*A61B 17/064* (2006.01)
*A61B 17/068* (2006.01)
(Continued)

(52) U.S. Cl.
CPC .......... *A61B 17/064* (2013.01); *A61B 17/068* (2013.01); *A61B 2017/00309* (2013.01);
(Continued)

(58) Field of Classification Search
CPC ................ A61B 17/064; A61B 17/068; A61B 2017/0039; A61B 2017/0647;
(Continued)

(56) References Cited

U.S. PATENT DOCUMENTS

| 4,991,763 A | 2/1991 | Storace |
|---|---|---|
| 5,114,065 A | 5/1992 | Storace |

(Continued)

FOREIGN PATENT DOCUMENTS

| DE | 103 00 787 | 9/2004 |
|---|---|---|
| EP | 2 260 775 A2 | 12/2010 |

(Continued)

OTHER PUBLICATIONS

International Search Report and Written Opinion for Application No. PCT/US2014/017640 dated Jul. 31, 2014.

(Continued)

*Primary Examiner* — Phong Son H Dang
(74) *Attorney, Agent, or Firm* — Wolf, Greenfield & Sacks, P.C.

(57) ABSTRACT

Surgical instruments and their methods of use are disclosed. In some embodiments, the surgical instrument may include a handle and an elongated shaft assembly extending distally from the handle. The surgical instrument may also include a fastener deployment system for deploying fasteners from the elongated shaft assembly including a reciprocating driveshaft disposed within the elongated shaft assembly. The driveshaft may include an internal channel and at least one guide surface shaped and arranged to maintain an orientation of at least one fastener in the channel of the driveshaft. In other embodiments, the fastener deployment system may include a follower disposed within the elongated shaft assembly for displacing one or more fasteners within the elongated shaft assembly towards a distal fastener deployment position.

19 Claims, 11 Drawing Sheets

Related U.S. Application Data continuation of application No. 13/826,979, filed on Mar. 14, 2013, now Pat. No. 9,427,230.

(51) Int. Cl.
    *A61B 17/00* (2006.01)
    *A61B 17/29* (2006.01)

(52) U.S. Cl.
    CPC .............. *A61B 2017/0647* (2013.01); *A61B 2017/2905* (2013.01); *A61B 2017/2927* (2013.01); *A61B 2017/2941* (2013.01)

(58) Field of Classification Search
    CPC .... A61B 2017/2905; A61B 2017/2927; A61B 2017/2941
    See application file for complete search history.

(56) References Cited

U.S. PATENT DOCUMENTS

| | | | |
|---|---|---|---|
| 5,258,010 A | 11/1993 | Green et al. | |
| 5,582,616 A | 12/1996 | Bolduc et al. | |
| 5,830,221 A | 11/1998 | Stein et al. | |
| 6,030,162 A | 2/2000 | Huebner | |
| 6,096,060 A | 8/2000 | Fitts et al. | |
| 6,228,098 B1 | 5/2001 | Kayan et al. | |
| 6,330,964 B1 | 12/2001 | Kayan et al. | |
| 6,368,322 B1 | 4/2002 | Luks et al. | |
| 6,450,391 B1 | 9/2002 | Kayan et al. | |
| 6,551,333 B2 | 4/2003 | Kuhns et al. | |
| 6,652,538 B2 | 11/2003 | Kayan et al. | |
| 6,779,701 B2 | 8/2004 | Bailly et al. | |
| 7,641,094 B2 | 1/2010 | Kayan et al. | |
| 7,670,362 B2 | 3/2010 | Zergiebel | |
| 7,758,612 B2 | 7/2010 | Shipp | |
| 7,828,820 B2 | 11/2010 | Stone et al. | |
| 7,862,573 B2 * | 1/2011 | Darois ................ | A61L 31/148 606/151 |
| 7,867,252 B2 | 1/2011 | Criscuolo et al. | |
| 7,931,660 B2 | 4/2011 | Aranyi et al. | |
| 8,002,811 B2 | 8/2011 | Corradi et al. | |
| 8,091,755 B2 | 1/2012 | Kayan et al. | |
| 8,216,272 B2 | 7/2012 | Shipp | |
| 8,382,773 B2 | 2/2013 | Whitfield et al. | |
| 8,414,628 B2 | 4/2013 | Melkent | |
| 8,663,244 B2 | 3/2014 | Reeser | |
| 9,186,138 B2 * | 11/2015 | Corradi ................ | B25B 13/481 |
| 9,427,230 B2 | 8/2016 | Ranucci et al. | |
| 9,474,530 B2 | 10/2016 | Ranucci et al. | |
| 9,615,830 B2 | 4/2017 | Ranucci et al. | |
| 10,251,642 B2 | 4/2019 | Ranucci et al. | |
| 2002/0068947 A1 | 6/2002 | Kuhns et al. | |
| 2003/0014060 A1 | 1/2003 | Wilson, Jr. et al. | |
| 2003/0233142 A1 * | 12/2003 | Morales ............ | A61B 17/0644 623/2.37 |
| 2004/0204723 A1 | 10/2004 | Kayan | |
| 2005/0187613 A1 | 8/2005 | Bolduc et al. | |
| 2005/0234478 A1 | 10/2005 | Wixey et al. | |
| 2005/0240222 A1 | 10/2005 | Shipp | |
| 2005/0267478 A1 | 12/2005 | Corradi et al. | |
| 2005/0267495 A1 * | 12/2005 | Ginn ................ | A61B 17/0057 606/151 |
| 2005/0273138 A1 | 12/2005 | To et al. | |
| 2006/0004364 A1 | 1/2006 | Green et al. | |
| 2006/0079115 A1 | 4/2006 | Aranyi et al. | |
| 2006/0079912 A1 | 4/2006 | Whitfield et al. | |
| 2006/0088398 A1 | 4/2006 | Lund | |
| 2006/0235437 A1 | 10/2006 | Vitali et al. | |
| 2007/0038220 A1 | 2/2007 | Shipp | |
| 2007/0088390 A1 | 4/2007 | Paz et al. | |
| 2007/0167950 A1 | 7/2007 | Tauro | |
| 2007/0250064 A1 | 10/2007 | Darois et al. | |
| 2008/0281336 A1 | 11/2008 | Zergiebel | |
| 2009/0204130 A1 | 8/2009 | Kantsevoy et al. | |
| 2010/0160931 A1 | 6/2010 | Karpiel et al. | |
| 2010/0204717 A1 | 8/2010 | Knodel | |
| 2010/0234886 A1 | 9/2010 | Godin | |
| 2010/0256442 A1 | 10/2010 | Ogdahl et al. | |
| 2010/0292712 A1 | 11/2010 | Nering et al. | |
| 2010/0312257 A1 | 12/2010 | Aranyi et al. | |
| 2010/0312258 A1 | 12/2010 | Shipp | |
| 2011/0006104 A1 | 1/2011 | Felix | |
| 2011/0071578 A1 | 3/2011 | Colesanti et al. | |
| 2011/0079627 A1 | 4/2011 | Cardinale et al. | |
| 2011/0112357 A1 | 5/2011 | Chapman et al. | |
| 2011/0172681 A1 | 7/2011 | Aranyi et al. | |
| 2011/0178534 A1 | 7/2011 | Whitman et al. | |
| 2011/0178535 A1 | 7/2011 | Whitman | |
| 2011/0178537 A1 | 7/2011 | Whitman | |
| 2012/0022557 A1 | 1/2012 | Cabiri et al. | |
| 2012/0022586 A1 | 1/2012 | Whitman et al. | |
| 2012/0029533 A1 | 2/2012 | Whitfield et al. | |
| 2012/0029538 A1 | 2/2012 | Reeser | |
| 2012/0085807 A1 | 4/2012 | Kayan et al. | |
| 2012/0122355 A1 | 5/2012 | Hemmi | |
| 2012/0241490 A1 | 9/2012 | Busch et al. | |
| 2014/0180323 A1 | 6/2014 | Shriver | |
| 2014/0236196 A1 * | 8/2014 | Colesanti ............ | A61B 17/064 606/151 |
| 2014/0243855 A1 | 8/2014 | Sholev et al. | |
| 2014/0257412 A1 | 9/2014 | Patty et al. | |
| 2014/0276964 A1 | 9/2014 | Ranucci et al. | |
| 2014/0276965 A1 | 9/2014 | Ranucci et al. | |
| 2014/0316446 A1 * | 10/2014 | Kayan ................ | A61B 17/064 606/151 |
| 2015/0005788 A1 | 1/2015 | Snifffin et al. | |
| 2016/0354081 A1 | 12/2016 | Ranucci et al. | |
| 2017/0020523 A1 | 1/2017 | Ranucci et al. | |
| 2017/0042657 A1 | 2/2017 | Criscuolo et al. | |

FOREIGN PATENT DOCUMENTS

| | | |
|---|---|---|
| EP | 2 012 677 | 11/2011 |
| JP | 2008-093431 A | 4/2008 |
| JP | 2009-261772 A | 11/2009 |
| JP | 2016-510646 A | 4/2016 |
| WO | 97/18761 A1 | 5/1997 |
| WO | 2004/112841 A2 | 12/2004 |
| WO | 2007/098512 A1 | 9/2007 |

OTHER PUBLICATIONS

International Preliminary Report on Patentability for Application No. PCT/US2014/017640 dated Sep. 24, 2015.

International Search Report and Written Opinion for Application No. PCT/US2014/017657 dated Jun. 12, 2014.

International Preliminary Report on Patentability for Application No. PCT/US2014/017657 dated Sep. 24, 2015.

* cited by examiner

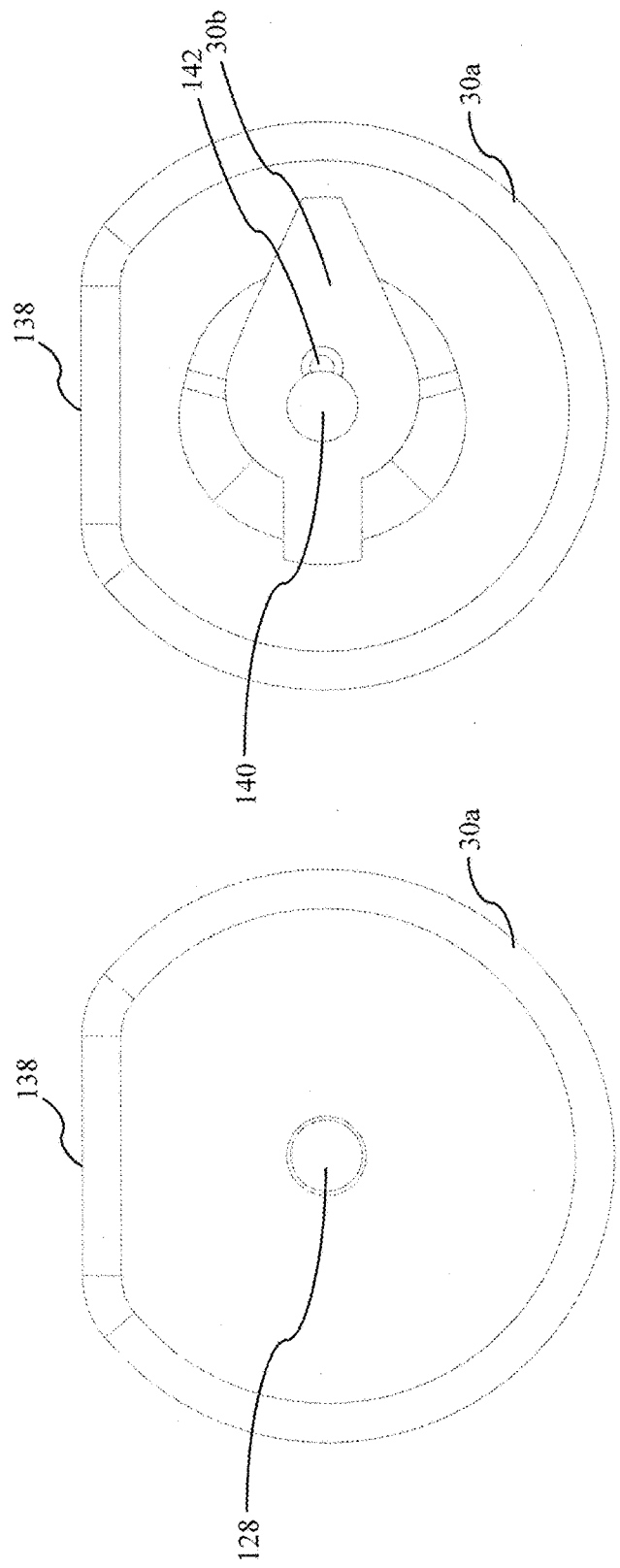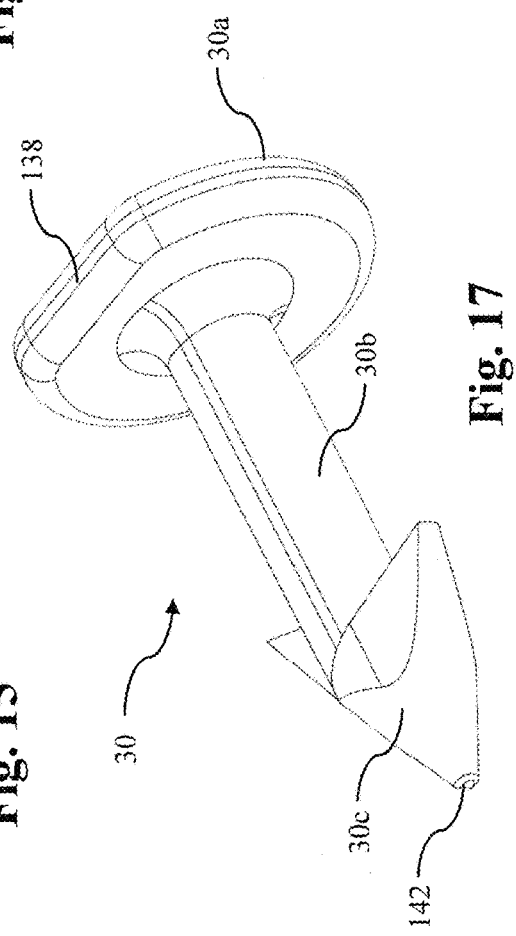

HANDLING OF FASTENERS WITHIN A SURGICAL INSTRUMENT

RELATED APPLICATIONS

This Application is a continuation of U.S. application Ser. No. 15/241,904, filed on Aug. 19, 2016, which is a continuation of U.S. application Ser. No. 13/826,979, filed on Mar. 14, 2013, both of which are herein incorporated by reference in their entirety.

FIELD

Disclosed embodiments are related to the handling of fasteners within a surgical instrument.

BACKGROUND

A surgical mesh fabric or other prosthetic repair fabric may be used to surgically repair a hernia. The prosthetic repair fabric is typically placed in an open procedure or laparoscopically. To secure the repair fabric in place, one or more fasteners may be deployed through the prosthetic repair fabric and into the underlying tissue. Oftentimes, surgical instruments used during the surgical repair of a hernia, or other appropriate procedure, include magazines, or other structures, that are capable of holding a plurality of fasteners for deployment from the surgical instrument. The inclusion of a plurality of fasteners within the surgical instrument may increase the speed of the procedure and may also reduce the need to remove and re-introduce the surgical instrument into a surgical field to provide additional fasteners.

SUMMARY

In one embodiment, a surgical instrument includes a handle and an elongated shaft assembly extending distally from the handle. The surgical instrument also includes a fastener deployment system including a driveshaft disposed within the elongated shaft assembly. The driveshaft includes at least one guide surface that at least partially defines an internal channel of the driveshaft. The at least one guide surface is shaped and arranged to maintain an orientation of at least one fastener in the channel of the driveshaft.

In another embodiment, a method for operating a surgical instrument includes: providing a surgical instrument including: a handle; an elongated shaft assembly extending distally from the handle; a fastener deployment system for deploying fasteners from the elongated shaft assembly including a driveshaft disposed within the elongated shaft assembly, wherein the driveshaft includes an internal channel; and at least one fastener disposed within the internal channel of the driveshaft; actuating the fastener deployment system to displace the driveshaft and deploy a second fastener from the elongated shaft assembly; and maintaining an orientation of the at least one fastener relative to the driveshaft during actuation of the fastener deployment system to deploy the second fastener.

In yet another embodiment, a surgical instrument includes a handle and an elongated shaft assembly extending distally from the handle. The surgical instrument also includes a fastener deployment system for deploying fasteners from the elongated shaft assembly including a driveshaft disposed within the elongated shaft assembly. The driveshaft includes an internal channel adapted and arranged to contain at least one fastener. A cross-section of the channel within a distally located portion of the driveshaft also includes a flat portion and a round portion.

In another embodiment, a surgical instrument includes a handle and an elongated shaft assembly extending distally from the handle. The surgical instrument also includes a fastener deployment system for deploying fasteners from the elongated shaft assembly and a follower disposed within the elongated shaft assembly and associated with one or more fasteners disposed within the elongated shaft assembly. Actuation of the fastener deployment system compresses the follower from a first length to a second length to apply a distally directed force to the one or more fasteners and displace the fasteners in a distal direction. During displacement of the one or more fasteners the follower expand from the second length to the first length.

In yet another embodiment, a surgical instrument includes a handle an elongated shaft assembly extending distally from the handle. The surgical instrument also includes a fastener deployment system for deploying fasteners from the elongated shaft assembly. The fastener deployment system includes a driveshaft disposed within the elongated shaft assembly and a follower disposed within the elongated shaft assembly and associated with the driveshaft. Distal displacement of the driveshaft deploys a fastener from the elongated shaft assembly and displaces the follower in a distal direction to displace one or more fasteners disposed in the elongated shaft assembly in a distal direction. A force applied to the deployed fastener by the driveshaft is greater than a force applied to the one or more fasteners by the follower.

In another embodiment, a surgical instrument includes a handle and an elongated shaft assembly extending distally from the handle. The surgical instrument also includes a fastener deployment system for deploying fasteners from the elongated shaft assembly and a follower disposed within the elongated shaft assembly for displacing one or more fasteners within the elongated shaft assembly in a distal direction. The follower applies a first force to the one or more fasteners prior to actuation of the fastener deployment system and a second force to the one or more fasteners after actuation of the fastener deployment system is begun to displace the one or more fasteners in the distal direction. The elongated shaft assembly is configured to apply a first restraining force and a second restraining force to the one or more fasteners. The first force is less than the first restraining force. Further, the second force is greater than the first restraining force and less than the second restraining force.

In yet another embodiment, a surgical instrument includes a handle and an elongated shaft assembly extending distally from the handle. A first restraining element and a second restraining element are associated with the elongated shaft assembly. The second restraining element is located distally from the first restraining element. The first restraining element and the second restraining element define a fastener deployment position. The surgical instrument also includes a fastener deployment system for deploying fasteners from the elongated shaft assembly. The fastener deployment system includes a driveshaft adapted and arranged to apply a deployment force to a fastener located in the fastener deployment position.

In another embodiment, a method of operating a surgical instrument includes: providing: a handle; an elongated shaft assembly extending distally from the handle; a fastener deployment system for deploying fasteners from the elongated shaft assembly; and a follower disposed within the elongated shaft assembly and associated with one or more fasteners disposed within the elongated shaft assembly; actuating the fastener deployment system to deploy a fastener from the elongated shaft assembly; distally displacing the follower to compress the follower from a first length to a second length to apply a distally directed force to one or more fasteners to displace the one or more fasteners in a distal direction, and wherein during displacement of the one or more fasteners the follower expands from the second length to the first length.

In yet another embodiment, a surgical instrument includes a handle and an elongated shaft assembly extending distally from the handle. The surgical instrument also includes a fastener deployment system for deploying fasteners from the elongated shaft assembly. The fastener deployment system includes a driveshaft. A follower is configured to displace a stack of fasteners and is disposed within the driveshaft. The follower and driveshaft form a walking beam assembly to sequentially displace the follower in a distal direction during each actuation cycle of the fastener deployment system.

In another embodiment, a surgical instrument includes a handle and an elongated shaft assembly extending distally from the handle. The surgical instrument also includes a fastener deployment system for deploying fasteners from the elongated shaft assembly. The fastener deployment system includes a driveshaft. An anti-backup element is associated with the driveshaft such that actuation of the fastener deployment system distally displaces the driveshaft and distal movement of the driveshaft extends the anti-backup element by a preselected length during each actuation cycle.

It should be appreciated that the foregoing concepts, and additional concepts discussed below, may be arranged in any suitable combination, as the present disclosure is not limited in this respect. The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 15 is a schematic top view of a fastener;

FIG. 16 is a schematic bottom view of the fastener depicted in FIG. 16;

FIG. 17 is a schematic perspective view of the fastener depicted in FIG. 16;

DETAILED DESCRIPTION

Figure 1:
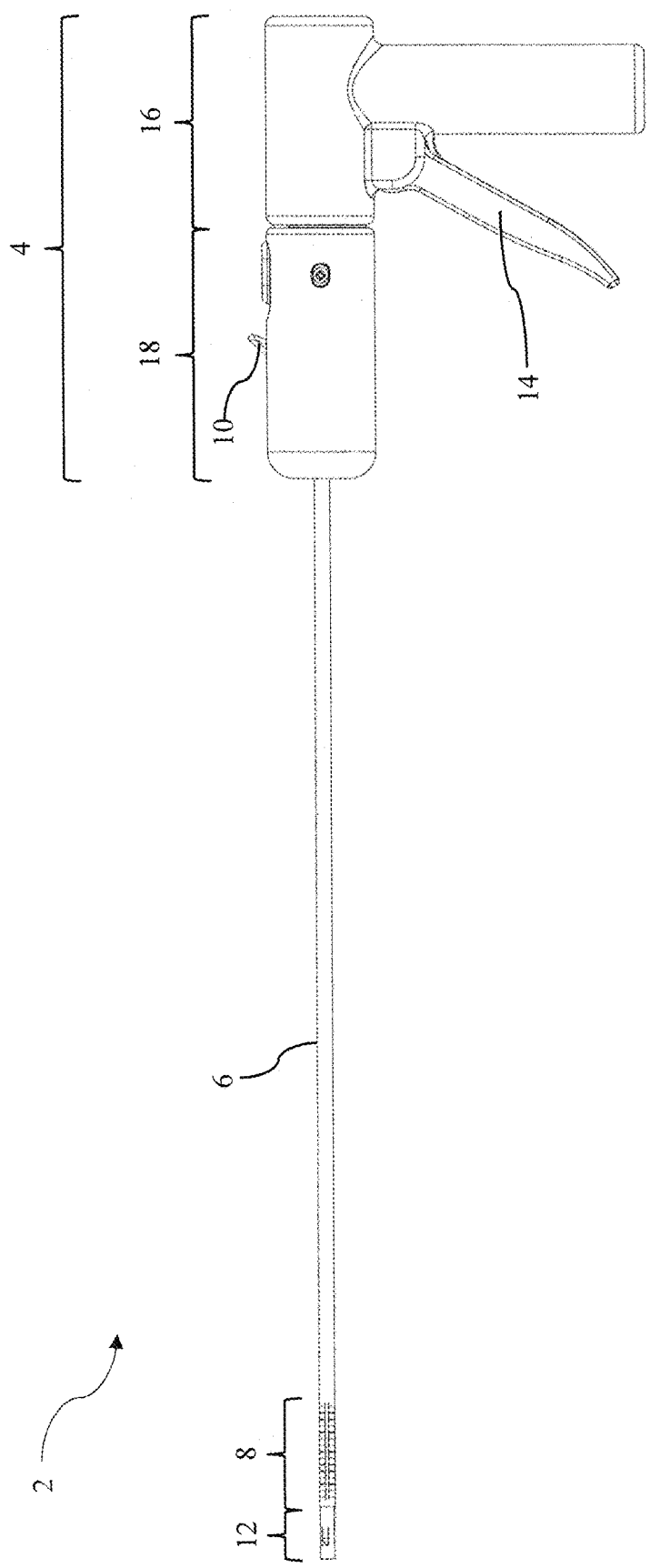
FIG. 1 is a schematic representation of an articulable surgical instrument.

The inventors have recognized that the application of excessive force to a stack of fasteners during actuation, as well as relative motion, such as rotation, between adjacent fasteners, may interfere with fastener deployment.

In view of the above, the inventors have recognized the benefits associated with providing a controlled force to a stack of fasteners to facilitate fastener deployment. Further, in some embodiments this force may be less than about the actuation force applied to a fastener located in a distal fastener deployment position. The inventors have also recognized several benefits associated with maintaining the orientation of the individual fasteners within the stack of fasteners and retaining a distal most fastener in a fastener deployment position. The above noted benefits may also lead to improved consistency in fastener deployment and surgical instrument operation.

In one embodiment, the surgical instrument may include a handle and an elongated shaft assembly extending distally from the handle. The elongated shaft assembly may include a distally located fastener deployment position from which a fastener may be deployed. The surgical instrument may also include a fastener deployment system to deploy a fastener from the fastener deployment position out of the distal end of the elongated shaft assembly. The fastener deployment system may be embodied in any number of ways. Further, in some embodiments, the fastener deployment system may include a magazine, or other appropriate structure for containing a plurality of fasteners. Depending upon the particular embodiment, the plurality of fasteners may be arranged as a nested stack of fasteners, though other arrangements are also envisioned. The fastener deployment system may also include a follower, or other appropriate component, that is associated with the stack of fasteners such that it displaces one or more fasteners towards the fastener deployment position during an actuation cycle of the fastener deployment system.

In addition to deploying the fastener, actuation of the fastener deployment system may also result in the distal displacement of the follower to distally displace the stack of fasteners towards the fastener deployment position and position a next distal most fastener in the fastener deployment position. The fastener deployment system may displace the follower in any appropriate fashion. For example, in one embodiment, the follower may be associated with a driveshaft of the fastener deployment system such that distal displacement of the driveshaft distally displaces the follower. Backwards movement of the follower may also be prevented through the use of an appropriate anti-backup element associated with the follower. Regardless of the specific manner in which the follower is displaced, the follower may be arranged and adapted to provide a controlled force to the stack of fasteners during displacement. The force applied to the stack of fasteners may be any appropriate force, and in one embodiment may be less than the actuation force applied to deploy a fastener from the fastener deployment position.

In certain embodiments, the follower may be constructed in any appropriate fashion such that it applies similar forces to the stack of fasteners during subsequent actuation cycles of the fastener deployment system. For example, the follower may include a driven element which is associated with the fastener deployment system such that actuation of the fastener deployment system distally displaces the driven element. The driven element may also be associated with a compressible elastic element which is associated with a pushing element. The elastic element may be adapted and arranged to provide a controlled force to the pushing element upon displacement of the driven element. The elastic element may comprise a coil spring, a conical spring, a pneumatic spring, an appropriately shaped component made of a compressible material (e.g. rubber), or any other appropriately shaped and sized compressible component capable of applying a force to the stack of fasteners when it is compressed. In some embodiments, in addition to providing a controllable force to the stack of fasteners, the elastic element may be sufficiently flexible to permit the follower to pass through an articulated portion of the elongated shaft assembly while still applying a force to the stack of fasteners. In such an embodiment, the driven element, elastic element, and pushing element may also be sized and shaped to pass through the elongated shaft assembly in both the straight and articulated configuration.

While the embodiments described herein refer to, and depict, the driven element, elastic element, and pushing element as separate components that are physically associated with one another, the current disclosure is not limited to the use of separate components. For example, in some embodiments, the driven element, elastic element, and pushing element may be provided as part of an integral component.

In some embodiments, the follower may be adapted to provide similar forces to the stack of fasteners during subsequent actuation cycles. While this may be accomplished in any number of ways, in one embodiment, the follower may operate in the following manner. Upon actuation of the fastener deployment system, the driven element may be distally displaced. The distal displacement of the driven element may compress the elastic element from a first length to a compressed second length. Subsequent to compressing the elastic element, the elastic element may expand from the compressed second length to the original first length. As the elastic element expands to the second length, the fasteners may be distally displaced along the elongated shaft assembly towards the fastener deployment position. In some embodiments, the difference between the first length and the second length may correspond to the length of one fastener. When the elastic element is in the expanded state corresponding to the first length, the elastic element may applying a first force to the pushing element and the stack of fasteners. Subsequently, when the elastic element is in the compressed state corresponding to the second length, the elastic element may applying a second force to the pushing element and the stack of fasteners. As would be expected for a compressed elastic element, the second force is greater than the first force. In some embodiments, the first force may be approximately zero. However, in other embodiments, it may be desirable to provide a distal bias to the stack of fasteners throughout the actuation cycle to prevent backwards movement of the stack of fasteners. In such an embodiment, the first force may greater than zero corresponding to an initial compression of the elastic element prior to actuation of the fastener deployment system.

In addition to the forces applied to the stack of fasteners by the follower, restraining forces may also be applied to the stack fasteners to prevent distal movement of the fasteners until the force applied by the follower exceeds a preselected threshold force. For example, a first restraining force may be applied to the stack of fasteners prior to, and during, actuation of the fastener deployment system. The first restraining force may be applied to the stack of fasteners to oppose the first force applied to the stack of fasteners by the follower. Consequently, prior to actuation of the fastener deployment system, the stack of fasteners may remain stationary within the elongated shaft assembly. However, during actuation, the elastic element may be compressed to a second compressed length to apply a greater force to the stack of fasteners as noted above. Once the applied force (e.g. the second force) is greater than the first restraining force, the stack of fasteners may be distally displaced by the follower to position the next fastener in the fastener deployment position. A second restraining force may subsequently be applied to restrain the stack of fasteners from additional distal movement during that actuation cycle.

Each of the noted restraining force may be provided by one or more restraining elements. Further, the restraining elements may be embodied in any number of fashions. For example, the restraining elements may include: one or more tabs that extend inwards and distally relative to the elongated shaft assembly; detent mechanisms; and other appropriate features. Further, the restraining elements may be integrally formed with the elongated shaft assembly, or the restraining elements may be formed separately and subsequently assembled with the elongated shaft assembly using any appropriate fashion including, but not limited to, welding, soldering, brazing, adhesives, mechanical couplings, fasteners, and interference fits.

In some embodiments, in addition to providing the restraining forces to the stack of fasteners, the restraining elements may also be used to define the fastener deployment position. For example, a head, or other appropriate feature, of a fastener may be retained between the first and second restraining elements to define the fastener deployment position.

In addition to providing a follower to control the forces applied to the stack of fasteners, as noted above, it may be desirable to provide a mechanism for maintaining the orientation of the fasteners within the elongated shaft assembly as the stack of fasteners is displaced towards the fastener deployment position by the follower. In one embodiment, a guide surface may be sized and shaped to interact with a corresponding surface on at least a portion of the fasteners to maintain the orientation of the fasteners as they move within the elongated shaft assembly. In some instances, the corresponding surface on the fastener may be shaped such that it is complementary both in shape and size to the guide surface. The guide surface may be positioned on any appropriate component of the elongated shaft assembly, or a component that is disposed within the elongated shaft assembly, that interacts with the fasteners as they are moved through the elongated shaft assembly. Further, the guide surface may extend along a distal portion of the component, a portion of the component corresponding to the stack of fasteners, or the entire length of the component as the current disclosure is not limited as to the location and extent of the guide surface.

It should be understood that the guide surface and the corresponding surfaces on the fasteners may include any combination of appropriate shapes and/or features that are capable of maintaining the orientation of the fasteners. For example, the guide surface and the corresponding surfaces on the fasteners might include: corresponding flats; a protrusion and corresponding groove; and other complementary arrangement as would be apparent to one of ordinary skill in the art.

In one particular embodiment, the fasteners may be disposed within an internal channel of a reciprocating driveshaft that reciprocates in a proximal and distal direction. Further, the guide surface might be incorporated with the interior surface of the channel. In such an embodiment, the guide surface may interact with the corresponding surface of the fasteners to maintain an orientation of the fasteners within the reciprocating driveshaft. During actuation of the fastener deployment system, the driveshaft may be moved in a distal direction to deploy a fastener prior to moving in a proximal direction in preparation for the next actuation cycle. During this reciprocating movement of the driveshaft, the driveshaft may be moved relative to the stack of fasteners. Additionally, during, or subsequent to deployment of the fastener, the stack of fasteners may be displaced towards the distal end of the driveshaft to position the next distal most fastener in the fastener deployment position using any appropriate biasing element. For example, the stack of fasteners might be displaced using a follower as described herein. As the stack fasteners are displaced towards the fastener deployment position, and as the driveshaft is moved relative to the stack of fasteners disposed therein, the guide surface may maintain the fasteners in a preselected orientation relative to one another and the driveshaft. As previously noted, maintaining the fasteners in a preselected orientation relative to one another and the driveshaft ensures proper alignment of the fasteners and may lower the necessary force to move the fasteners through an articulated portion of the elongated shaft assembly.

For the sake of clarity, the currently disclosed embodiments are directed to a laparoscopic device. However, the current disclosure is not limited to laparoscopic devices. Instead, the currently disclosed followers, restraining elements, and guide surfaces could be used in any appropriate device for the deployment of a fastener into tissue. For example, any of the currently disclosed components, or combination of disclosed components, could be incorporated into an endoscopic device, a borescopic device, a catheter, a surgical instrument for use in "open" procedures, or any other appropriate surgical instrument. Additionally, the surgical instrument may be loaded with one or more fasteners prior to being provided to an end user, or it may be constructed to allow the user to load the instrument with one or more fasteners. Further, while the various embodiments depicted herein are described as being used with a specific fastener, any appropriate fastener could be used with the currently disclosed embodiments including a tack, a clip, a staple, a pin, a tissue anchor, a bone anchor, or any other appropriate type of fastener.

Turning now to the figures, specific embodiments of the surgical instrument are described.

FIG. 1 presents one embodiment of a surgical instrument 2. The surgical instrument includes a handle 4 and an elongated shaft assembly 6 extending distally from the handle 4. In addition to fasteners being deployed from a distal end of the elongated shaft assembly, the elongated shaft assembly 6 may include an articulable portion 8. The surgical instrument 2 may also include a trigger 14 to actuate an associated fastener deployment system 15, see FIG. 2, and deploy a fastener into tissue.

The articulable portion 8 may be articulated between a first position, such as an unarticulated (i.e. straight) position, and a second position, such as a fully articulated position, using the articulation control 10. In some embodiments, the articulable portion 8 may be articulated only between the first and second positions. In other embodiments, the articulable portion 8 may be articulated to one or more preselected articulated positions, or any arbitrary (i.e. not preselected) articulated position as the current disclosure is not limited in this fashion. Further, depending upon the embodiment, the articulable portion 8 may only be articulated in one direction, or it may be articulated in two directions. For example, the articulable portion 8 may be articulated between approximately 0° and 90°, 0° and 45°, −90° and 90°, −180° and 180° or any other appropriate range of angles. In addition, in some embodiments the articulable portion 8 may articulate about two different axes (e.g. articulation in the horizontal direction and vertical direction).

Figure 12:
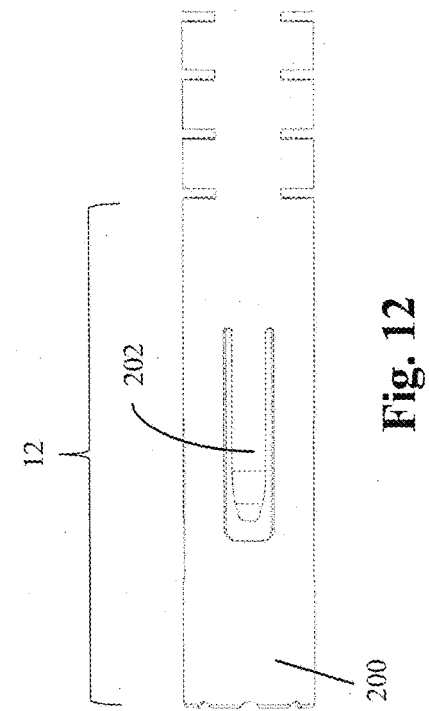
FIG. 12 is a schematic side view of the rigid straight portion depicted in FIG. 11 rotated 120°.

In some embodiments, it may be desirable to rotate the elongated shaft assembly 6 to facilitate positioning of the distal tip. One such embodiment is depicted in FIGS. 1 and 12. The rotation of the elongated shaft assembly 6 may be provided in any appropriate manner. For example, the elongated shaft assembly 6 may simply be adapted to be rotatable to at least a portion of the handle 4. Alternatively, a portion of the handle 4 including the elongated shaft assembly 6 may be rotatable relative to another portion of the handle 4, such as the portion including the grip. One such embodiment is depicted in FIG. 1. In the depicted embodiment, the surgical instrument 2 includes a first handle portion 16 and a second handle portion 18 including the elongated shaft assembly 6. The first and second handle portions 16 and 18 may be constructed and arranged in any appropriate fashion to be rotatable relative to one another. It should be understood that while a surgical instrument including a rotatable elongated shaft assembly 6 or handle 4 is depicted in the figures, a surgical instrument including a unitary handle and/or an elongated shaft assembly 6 that is stationary relative to the handle are also possible as the current disclosure is not limited in this manner.

In certain applications, it may be advantageous to include a rigid straight portion 12 distally located from the articulable portion 8. For example, and without wishing to be bound by theory, when a driveshaft applies a force to a fastener as it goes around a curve, the force applied by the driveshaft to a proximal portion of the fastener may not be aligned with the deployment direction of the fastener. This may result in a portion of the applied force being directed against a side of the elongated shaft assembly 6. In contrast, when a driveshaft applies a force to a fastener along a straight section, the applied force is aligned with the deployment direction of the fastener. Thus, including a rigid straight portion 12 that distally extends from the articulable portion 8 for a given length may enable the driveshaft to apply a reduced actuation force to deploy the fastener since the applied actuation force may be aligned with the deployment direction. Further, applying an actuation force that is aligned with the deployment direction may also improve the consistency of fastener deployment as the surgical instrument is varied between different articulation angles. In addition to the benefits noted above, the rigid straight portion 12 may also incorporate other components or features to aid in the positioning and deployment of a fastener from the surgical instrument. While a surgical instrument 2 including a distal rigid straight portion 12 has been described herein, and depicted in figures, it should be understood that embodiments are also envisioned in which the articulable portion 8 extends all the way to the distal end of the elongated shaft assembly 6 such that the surgical instrument does not include a distal rigid straight portion.

Figure 2:
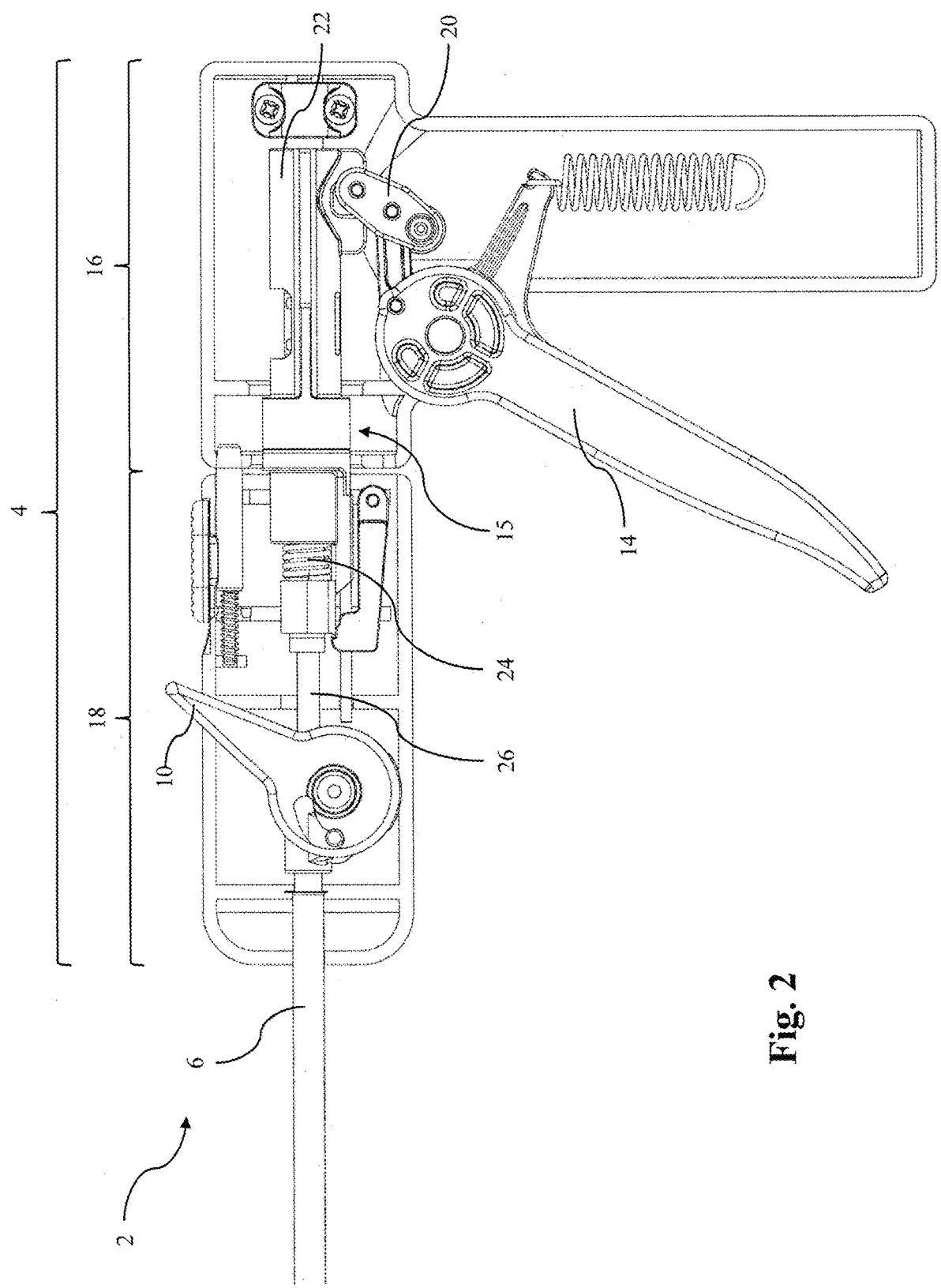
FIG. 2 is a schematic representation of the interior of the surgical instrument handle of FIG. 1.

As noted previously, the surgical instrument 2 may also include a fastener deployment system 15 as depicted in FIG. 2. The fastener deployment system 15 may be embodied in any number of different ways. However, in the particular embodiment depicted in FIG. 2 the fastener deployment system may include a trigger 14, a rigid linkage 20, a shuttle 22, a power assist device 24, and a reciprocating driveshaft 26 as well as other components that are not depicted. Actuation of the trigger 14 may distally displace the rigid linkage 20 to distally displace the shuttle 20 and store energy in the power assist device 24. After a preselected amount of actuation, the power assist device 24 may release the stored energy to distally accelerate the driveshaft 26 and deploy a fastener from the distal end of the elongated shaft assembly 6.

While a particular power assist device 24 is depicted, the power assist device 24 may correspond to any appropriate construction capable of aiding in deploying a fastener from the elongated shaft assembly 6 of the surgical instrument. Depending on the particular embodiment, the power assist device 24 may supply all of the power necessary to deploy a fastener in response to actuation of the trigger 14, or it may only supply a portion of the power necessary to deploy a fastener. In one specific embodiment, the power assist device 24 may correspond to the power assist device disclosed in application Ser. No. 13/804,043 entitled POWER ASSIST DEVICE FOR A SURGICAL INSTRUMENT filed on the same day as the current application. While a surgical instrument including a power assist device has been depicted, in some embodiments, the surgical instrument 2 may not include a power assist device, in which case actuation of the trigger 12 might displace driveshaft 26, either directly or indirectly through the use of an appropriate transmission, to deploy a fastener from a distal end of the elongated shaft assembly 6.

Figure 3:
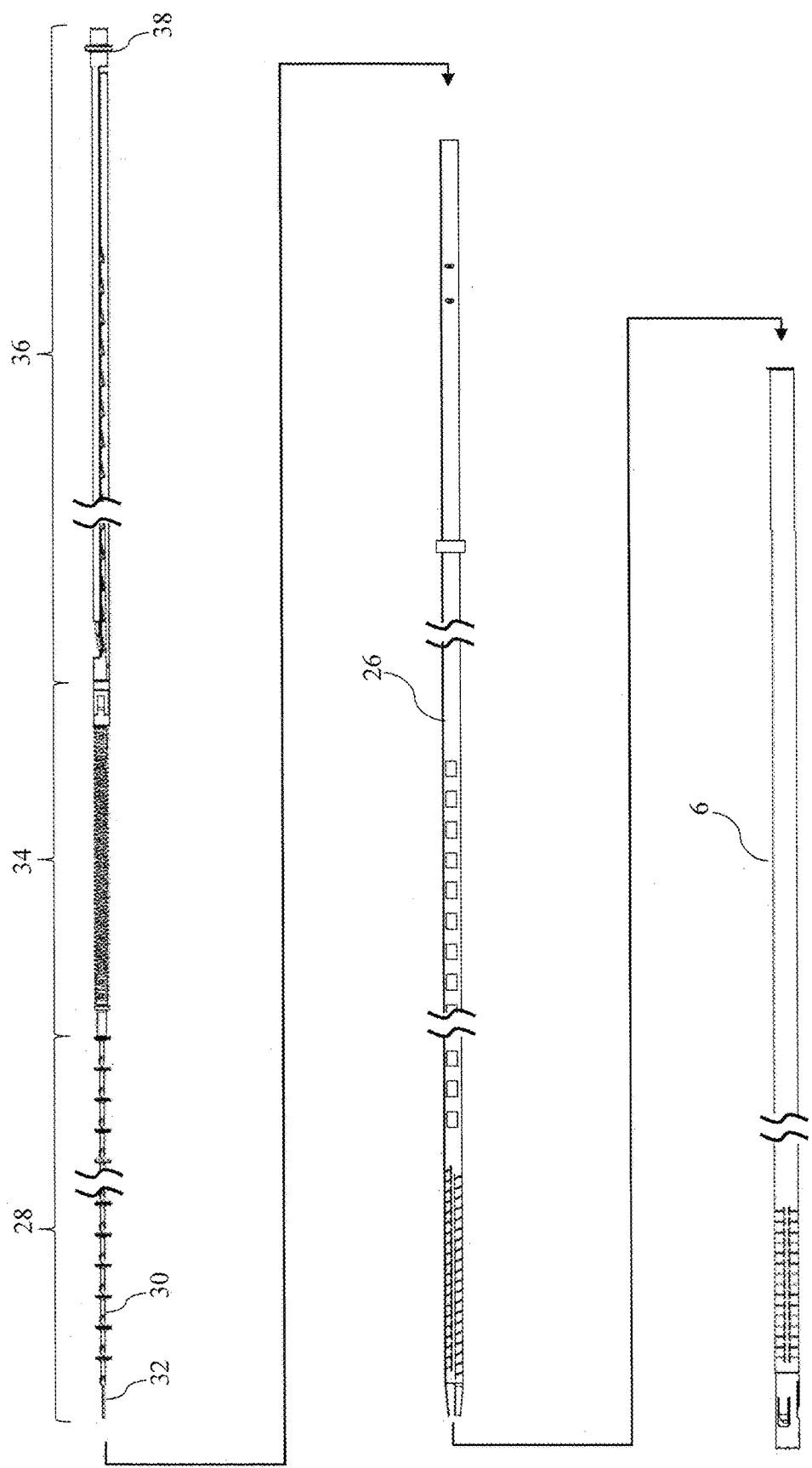
FIG. 3 is a schematic exploded view of the elongated shaft assembly and the components disposed within the channel of the elongated shaft assembly.

FIG. 3 presents an exploded view of one embodiment of the elongated shaft assembly 6 and the various components disposed within the elongated shaft assembly. In the depicted embodiment, the driveshaft 26 is located within the elongated shaft assembly 6. As illustrated by FIGS. 2 and 3, when disposed within the elongated shaft assembly 6, the driveshaft 26 extends proximally from the elongated shaft assembly 6 into the handle 4. The surgical instrument also includes a stack of fasteners 28, a follower 34, and an anti-backup element disposed within an internal channel of the driveshaft 26. The stack of fasteners 28 may include one or more fasteners 30, and in some instances may be a plurality of fasteners 30.

In addition to the above components, the surgical instrument may also include a fastener guide 32 to help maintain the alignment of the stack of fasteners 28, the follower 34, and the anti-backup element 36 within the internal channel of the driveshaft 26. While any appropriate structure may be used, in the depicted embodiment, the fastener guide 32 is a distally extending wire positioned in approximately the center of the channel of the driveshaft. The fastener guide 32 may be retained within the channel in any appropriate fashion. For example, the fastener guide 32 may be attached to a portion of the anti-backup element 36, a portion of the handle 4, or any other appropriate structure. Further, the faster guide 32 may be attached using any appropriate method including, but not limited to, adhesives, mechanical interference, clamping, soldering, brazing, and welding.

Upon actuation of the trigger, the fastener deployment system may be actuated resulting in a distal displacement of the driveshaft 26. As described in more detail below, a distal displacement of the driveshaft 26 deploys a distal most fastener located in the fastener deployment position. The driveshaft 26 also distally displaces the follower 34 to displace the stack of fasteners 28 and position the next distal most fastener in the fastener deployment position. The follower 34 and anti-backup element 36 may be associated such that a distal displacement of the following 34 results in the anti-backup element extending in the distal direction to prevent a proximal movement of the follower 34. After deployment of a fastener, and positioning of the next fastener in the fastener deployment position, the driveshaft 26 may be moved in a proximal direction to prepare the surgical instrument for the next actuation while preventing proximal movement of the stack of fasteners 28, the follower 34, and the anti-backup element 36.

Figures 4, 5, 6:
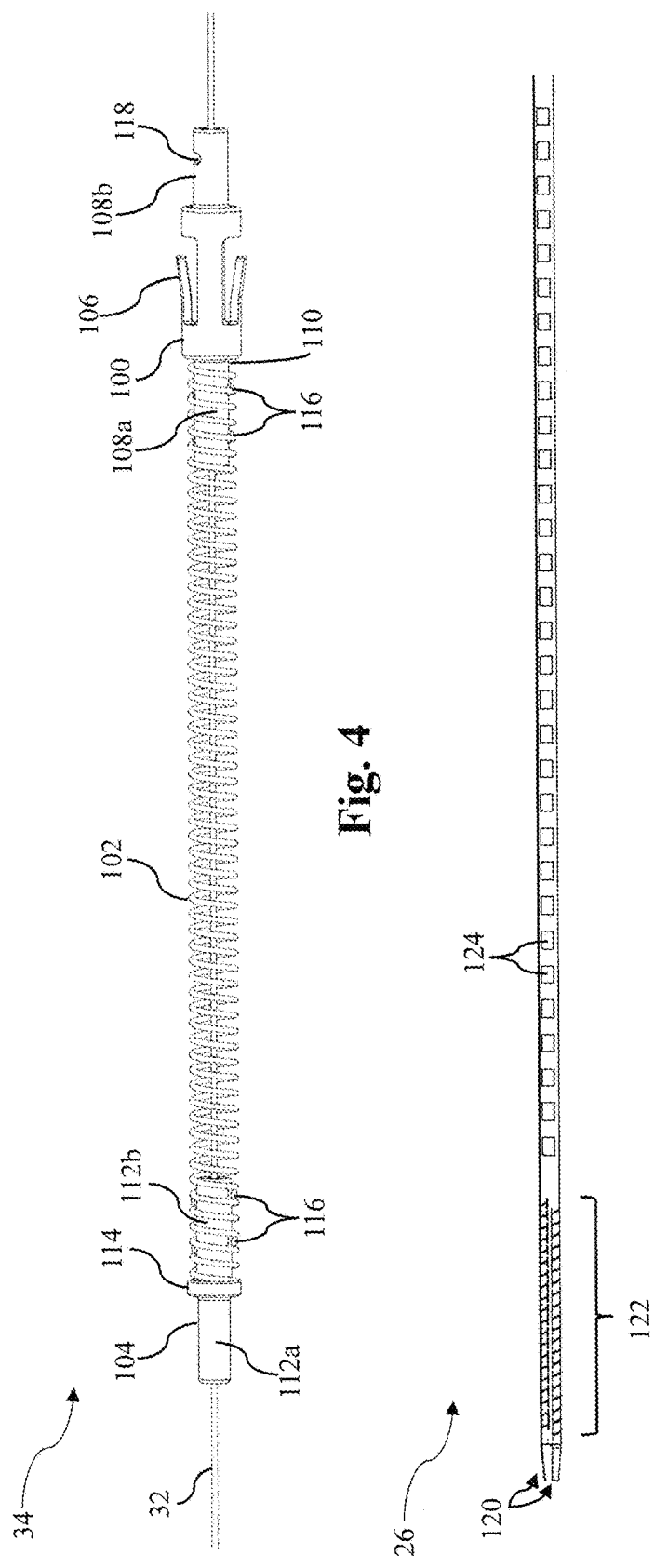
FIG. 4 is a schematic representation of a follower.
FIG. 5 is a schematic representation of a distal portion of the reciprocating driveshaft.
FIG. 6 is a schematic cross-sectional view of the follower located within the driveshaft.

The interaction between the follower 34 and the driveshaft 26 is depicted in FIGS. 4-6.

In the depicted embodiment, the follower 34 includes a driven element 100, an elastic element 102, and a pushing element 104. The driven element 100 is adapted to interact with the driveshaft 26 to displace the follower 34 in a distal direction. The driven element 100 includes tabs 106 which interact with openings 124 on the driveshaft 26. The tabs 106 may be flexible and extend outwards and distally from the driven element 100. In addition, the tabs 106 may be sized, shaped, and arranged such that the tabs 106 may be disposed within the openings 124 as the driven element 100 is distally moved through driveshaft 26. Driven element 100 may also include a distal portion 108a as well as a shoulder 110. The distal portion 108a and the shoulder 110 may be sized and shaped to retain a distal end of the elastic element 102 on the distal portion 108a. The distal portion 108a may also include one or more retention features 116. The depicted retention features 116 are protrusions located on the distal portion 108a that interfere with the elastic element 102 to retain the elastic element thereon. Alternatively, the elastic element 102 might be retained on the driven element 100 using any appropriate method including, but not limited to, mechanical interference, interlocking features, adhesives, welding, soldering, and brazing. The driven element 100 may also include a coupling 118 located on a proximal portion 108b. The coupling 118 may be adapted and arranged to attach the follower 34 to the anti-backup element 36.

The depicted elastic element 102 is a coil spring that extends between the driven element 100 and the pushing element 104. As noted above, while a coil spring has been depicted, other springs and appropriate components could be used in place of a coil spring. Regardless of the specific component used as the elastic element 102, the elastic element 102 may be sized, shaped, and arranged to be associated with both the driven element 100 and the pushing element 104. Further, due to the use of a spring, or other appropriate compressible component, as the driven element is moved in a distal direction, the elastic element 102 is compressed to apply a force to the pushing element 104. Larger displacements of the driven element 100 prior to movement of the pushing element 104 may result in larger compressions of the elastic element 102 and correspondingly larger forces. Depending upon the particular embodiment, the elastic element 102 may exhibit a linear force to displacement relationship, or a nonlinear force to displacement relationship, as the current disclosure is not limited in this fashion.

Similar to the driven element 100, pushing element 104 may include a proximal portion 112b and a shoulder 114 that are sized and shaped to retain a distal end of the elastic element 102. The pushing element 104 may also include one or more retention features 116 for retaining the elastic element 102 similar to those described above for the driven element 100. The pushing element 104 may also include a distal portion 112a that is adapted and arranged to apply a force to the most proximally located fastener of the fastener stack. In some embodiments, the distal portion 112a may directly contact at least the proximal most fastener in the stack of fasteners, though embodiments in which the distal portion 112a indirectly applies a force to the stack of fasteners are also envisioned.

As depicted in FIG. 5, the driveshaft 26 may include one or more fastener driving elements 120 located on the distal end of the driveshaft 26. In some embodiments, the fastener driving element 120 may be one or more flexible tabs that extend inwards and distally from the distal end of the driveshaft 26. The fastener driving elements 120 may be adapted to apply a force to a fastener located in the fastener deployment position to deploy the fastener from the distal end of the elongated shaft assembly. The driveshaft may also include a flexible portion 122 to accommodate movement of the reciprocating driveshaft through the articulable portion of the elongated shaft assembly. In the depicted embodiment, the flexible portion 122 is formed by providing a pattern of slots, or cuts, in the driveshaft 26. As noted above, the driveshaft 26 may also include openings 124 that are sized and shaped to accommodate the tabs 106 of the driven element 100 in an expanded position. One or more sets of openings 124 may be axially spaced along one or more surfaces of the driveshaft 124. In some embodiments, the axial spacing between the openings 124 may correspond to the length of a single fastener. In the current embodiment, two sets of openings 124 extend along opposite sides of the driveshaft 26 to accommodate both of the tabs 106 of the driven element 100. The openings 124 may extend along the entirety of driveshaft 24, or as depicted in the figures, the openings 124 may extend along a portion of the driveshaft 24 corresponding to an initial proximal position of the follower 34 and a final distal position of the follower 34 after all of the fasteners have been deployed from the surgical instrument.

Having described the corresponding features on the driveshaft 26 and the follower 34, the interactions of these two components during actuation in one possible embodiment will now be described, see FIG. 6. Prior to actuation, the tabs 106 of the driven element 100 may be located in the expanded state in any one of the corresponding openings 124 of the driveshaft 26. While the tabs 106 are in the expanded state within a corresponding opening 124, a proximal portion of the driveshaft 124a, such as a proximal edge of the opening may be axially aligned with a proximal aspect 106a of a tab 106. Consequently, as the driveshaft 26 is moved in a distal direction during actuation, the proximal driveshaft portion 124a applies a distally directed force to the proximal aspect 106a of the tabs 106 resulting in a distal displacement of the driven element 100. After the fastener has been deployed, the driveshaft 26 is subsequently moved in a proximal direction. During the proximal movement of the driveshaft 26, a distal portion of the shaft 124b, such as a distal edge of the openings 124, may be drawn over an exterior aspect 106b, such as an exterior surface, of the tabs. As described in more detail below, the driven element 100 may be prevented from moving backwards during the relative movement of the driveshaft 26 and the driven element 100. Further, as noted above, the tabs 106 are flexible. Thus, as the distal driveshaft portion 124b is drawn over the exterior aspect 106b of the tabs, the tabs 106 may be displaced inwards and out of the openings 124 to permit the relative movement of the driven element 100 and the driveshaft 26. The proximal displacement of the driveshaft 26 may be continued until the tabs 106 are aligned with the next distally located set of openings 124 and the tabs 106 are in the expanded state within the openings 124. Subsequent actuation cycles may result in the driven element 100 progressively moving in a distal direction as the driven element 100 engages with the next corresponding set of openings 124 of the driveshaft. In view of the above, the driven element 100 of the follower 34 and the driveshaft 26 may be described as forming two separate components of a walking beam assembly that is configured to sequentially displace the follower 34 in a distal direction during each actuation cycle of the fastener deployment system.

Figure 7A:
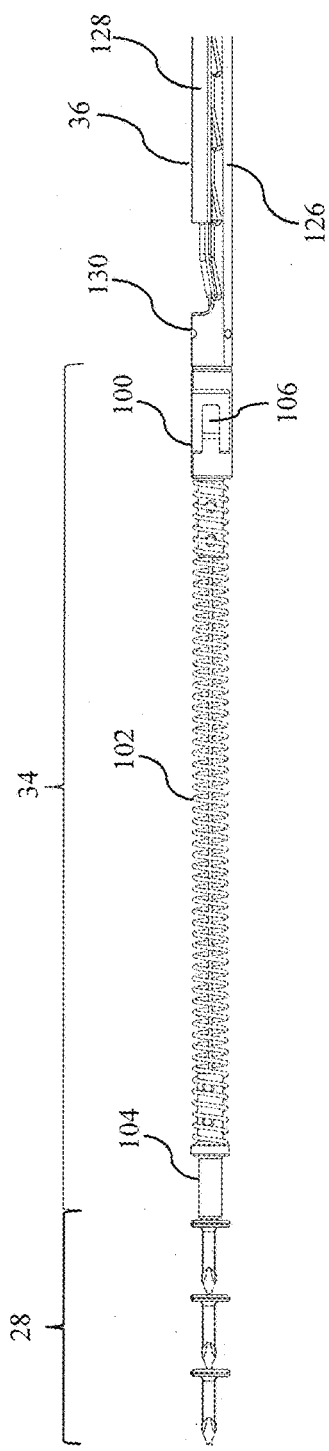
FIG. 7A is a schematic representation of a stack of fasteners and the follower in an unbiased position.
Figure 7B:
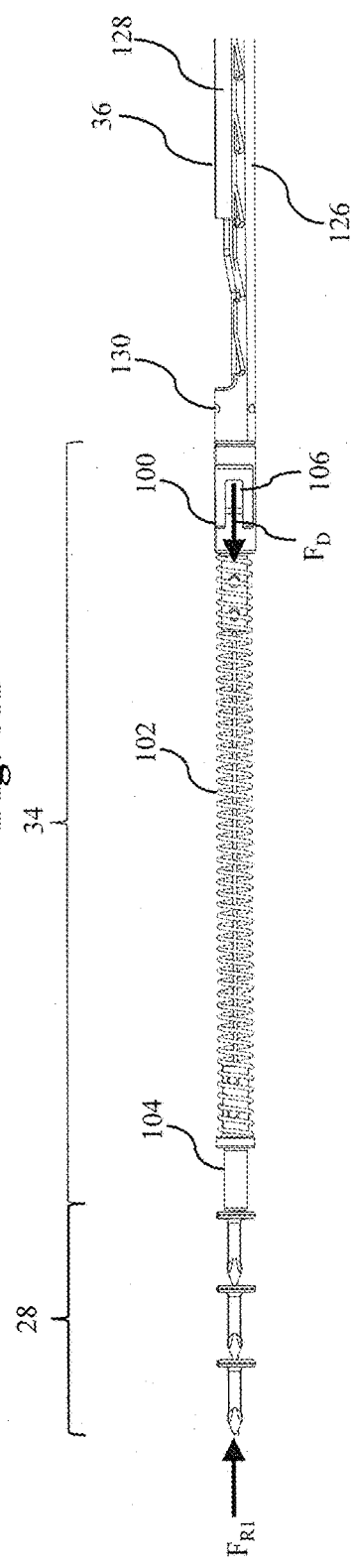
FIG. 7B is a schematic representation of the stack of fasteners and the follower of FIG. 6 with a biasing force applied.

FIGS. 7A-7B depict the interaction of the stack of fasteners 28, the follower 34, and the anti-backup element 36 during an actuation cycle of the fastener deployment system. As illustrated in the figures, the pushing element 104 may be in contact with a proximally located fastener of the fastener stack 28. The elastic element 102 may also be associated with a proximal portion of the pushing element 104 and a distal portion of the driven element 100. The driven element 100 may be coupled to a rack arm 126 of the anti-backup element 36 by a coupling 130. The driven element 100 and rack arm 126 may be coupled in such a manner that distal movement of the driven element 100 may result in the distal extension of the rack arm 126 relative to a pawl arm 128 of the anti-backup element 36. Thus, as the follower 34 is distally displaced through the elongated shaft assembly, the anti-backup element 36 correspondingly elongates. Consequently proximal movement of the follower 34 may be prevented by the anti-backup element 36 throughout the actuation cycle. As depicted in the figures, coupling 130 corresponds to a pin connection. However, any appropriate connection might be used including, but not limited to, interlocking mechanical features, a set screw, fasteners, adhesives, welding, brazing, and interference fits.

Prior to actuation, as depicted in FIG. 7A, the elastic element 102 of the follower 34 is in the expanded state corresponding to the first length and may apply a first distally directed force to the distally located pushing element 104 and the stack of fasteners 28. The follower 34 and the stack of fasteners 28 are prevented from moving in a distal direction by the anti-backup element 36. In the depicted embodiment, the anti-backup element 36 includes a rack arm 126 which may be moved in the distal direction, and a pawl arm 128 which remains stationary during actuation of the surgical instrument.

Figure 7C:
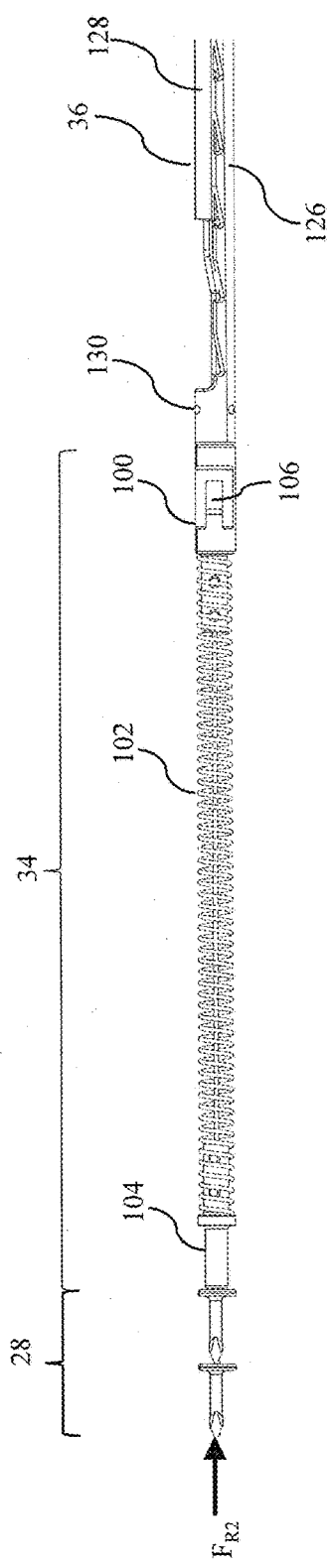
FIG. 7C is a schematic representation of the stack of fasteners and the follower of FIG. 6 after the stack of fasteners have been distally displaced.

Referring to FIG. 7B, as the fastener deployment system is actuated, the driveshaft, not depicted, may apply a force $F_D$ to the tabs 106 of the driven element 100 which drives the driven element 100 in a distal direction as described above. A proximally directed first restraining force $F_{R1}$ may be applied to the stack of fasteners 28. Initially, the first restraining force $F_{R1}$ may be equal to force $F_D$. Thus, during the initial portions of actuation, the stack of fasteners 28 may remain stationary resulting in the compression of elastic element 102 between the pushing element 104 and the driven element 100. As actuation continues, the force applied to the driven element 100 may continue to increase as the elastic element 102 is further compressed. This continued compression of the elastic element 102 applies an increasing distally directed force to the stack of fasteners 28. At some point during actuation, the spring may be compressed to a second length corresponding to the elastic element 102 applying a second distally directed force to the pushing element 104 and the associated stack of fasteners 28. This second distally directed force may be greater than the first restraining force $F_{R1}$ resulting in the expansion of the elastic element 102 and distal displacement of the pushing element 104 and associated stack of fasteners 28, see FIGS. 7B-7C.

As depicted by the figures, the elastic element 102 continues to expand from the second length to the first length as the stack of fasteners 28 is displaced in the distal direction. As the elastic element 102 approaches the expanded first length, a proximally directed second restraining force $F_{R2}$ may be applied to the stack of fasteners 28 to prevent further distal movement of the stack of fasteners. The second restraining force $F_{R2}$ may be greater than the first restraining force to oppose both the force applied to the stack of fasteners 28 by the elastic element 102 as well as possible kinetic energy stored in the stack of fasteners 28 and follower 34 as they are being distally displaced. The second restraining force may also be less than the actuation force to deploy a fastener from the elongated shaft assembly. In some embodiments, the second restraining force $F_{R2}$ may be applied once a distally located fastener of the stack fasteners 20 has been positioned in the fastener appointment position. After the stack of fasteners 28 has been distally displaced and the fastener deployment system has been reset, the surgical instrument may be actuated again resulting in further distal displacement of the follower 34 and the associated stack of fasteners 28.

Figure 8A:
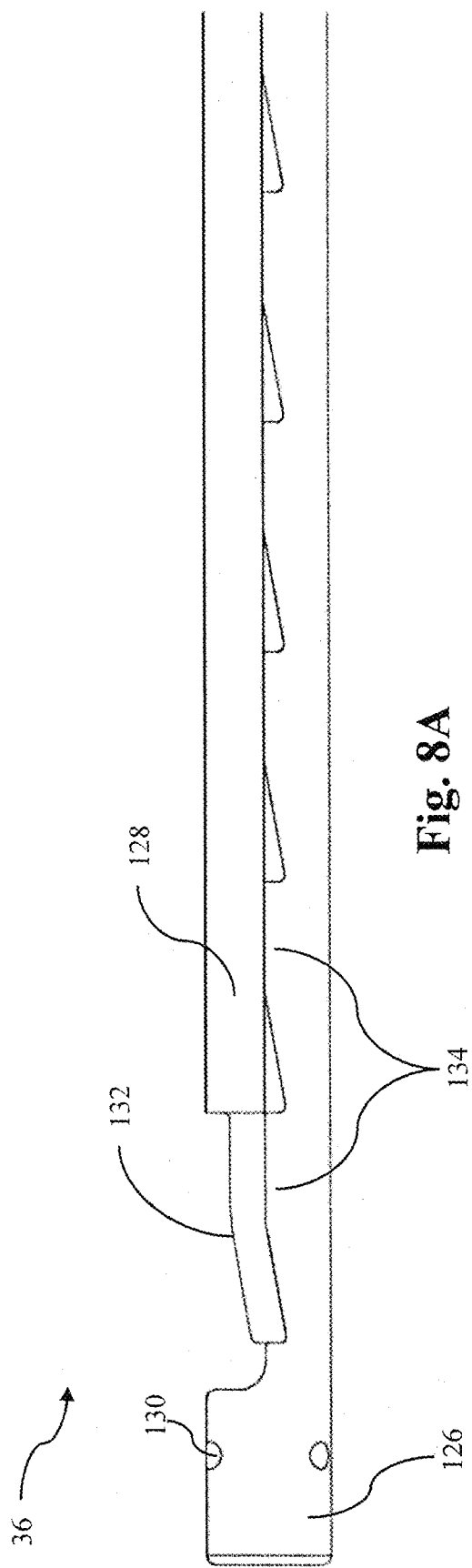
FIG. 8A is a schematic representation of a distal portion of the anti-backup mechanism.
Figure 8B:
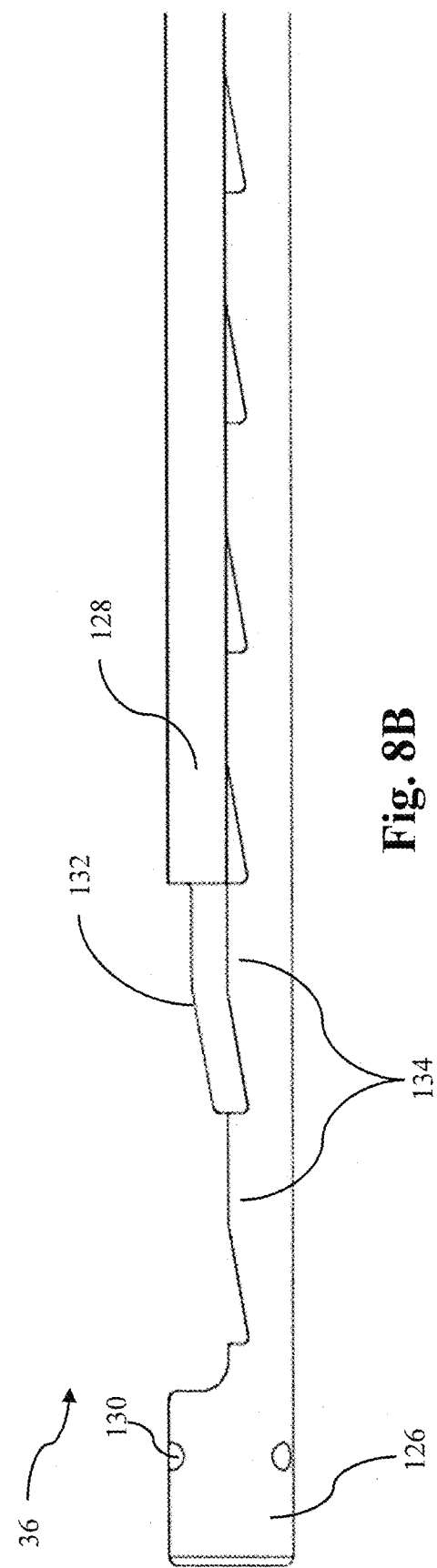
FIG. 8B is a schematic representation of the anti-backup mechanism depicted in FIG. 8A after one actuation cycle.
Figure 11:
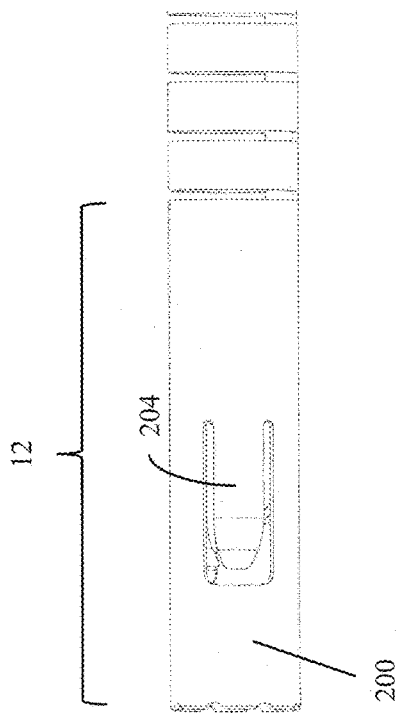
FIG. 11 is a schematic side view of the rigid straight portion depicted in FIG. 9.

In addition to displacement of the follower 34 and the associated stack of fasteners 28, actuation of the fastener deployment system may also result in an extension of the anti-backup element 36 as noted above. More specifically, due to the driven element 100 and the rack arm 126 being coupled, distal displacement of the driven element 100 may result in a corresponding distal displacement of the rack arm 126 relative to the pawl arm 128. The distal movement of the rack arm 126 may extend the anti-backup element 36 in a distal direction to prevent backwards movement of the driven element 100 after the stack of fasteners 28 has been distally displaced. The interactions of the rack arm 126 and the pawl arm 128 are illustrated in more detail in FIGS. 8A and 8B. Teeth 134 may be spaced along the axial length of the rack arm 126. A corresponding pawl 132 may be positioned on a distal portion of the pawl arm 128. The pawl 132 and the corresponding teeth 134 may be adapted and arranged to permit distal movement of the rack arm 126 in response to distal movement of the driven element. The pawl 132 and the corresponding teeth 134 may also be adapted and arranged to prevent proximal movement of the rack arm 126. In one embodiment, the distance between the teeth 134 may be approximately equal to one fastener length. However, embodiments in which the distance between teeth 134 is a fraction of a fastener length, or greater than a fastener length, are also envisioned. In addition to the above, while a rack and pawl system have been depicted for the anti-backup element 36, any appropriate mechanism capable of preventing backwards movement of the follower and the stack fasteners could be used.

Figure 9:
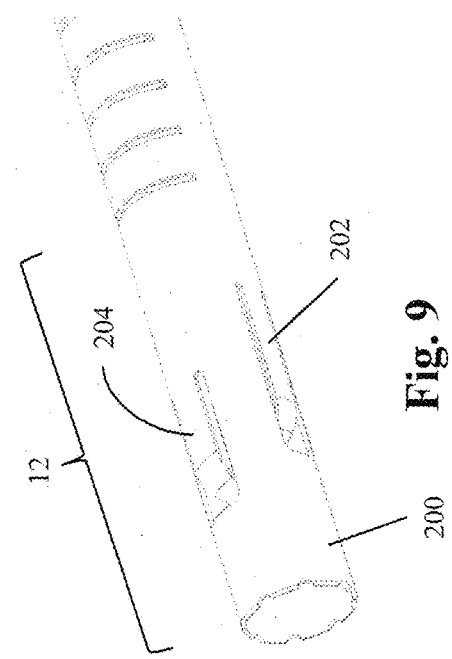
FIG. 9 is a schematic perspective view of the rigid straight portion including first and second restraining elements.
Figure 10:
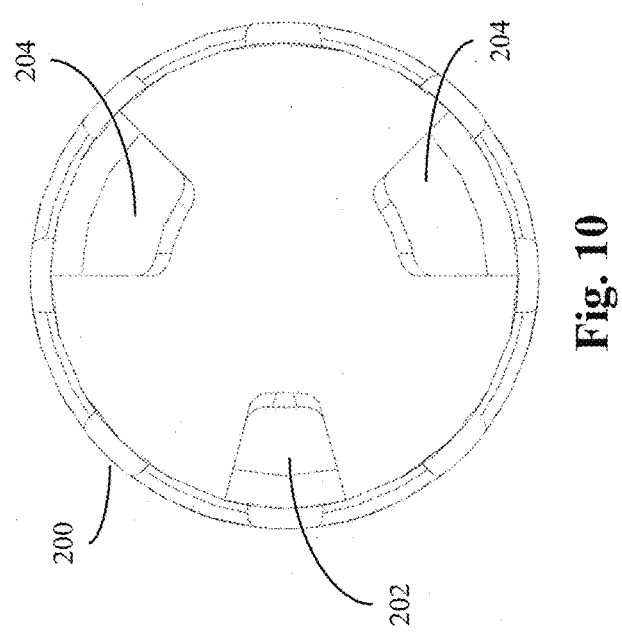
FIG. 10 is a schematic end view of the rigid straight portion depicted in FIG. 9.

FIGS. 9-12 depict an inner tubular member 200 which is a component of the elongated shaft assembly 6. The inner tubular member 200 includes the rigid straight portion 12 which forms the distal end of the elongated shaft assembly 6. The inner tubular member may also include one or more first restraining elements 202 and one or more second restraining elements 204 located within the rigid straight portion 12. As depicted in FIG. 9, the two second restraining elements 204 are distally located relative to a first restraining elements 202. The first restraining element may be adapted and arranged to provide the first restraining force to the stack of fasteners during actuation. Correspondingly, the second restraining elements 204 may be adapted and arranged to provide the second restraining force to the stack fasteners during actuation. As noted previously, the first restraining force may be less than the second restraining force. The different restraining forces may be provided in any number of ways as the current disclosure is not limited to the manner in which the restraining forces are applied to the stack of fasteners. In some embodiments the restraining elements may be integrally formed with elongated shaft assembly, or a component of the elongated shaft assembly. Alternatively, the restraining elements may be formed separately and assembled with elongated shaft assembly in any appropriate fashion including, but not limited to, welding, soldering, brazing, adhesives, interference fits, and fasteners.

The different first and second restraining forces may be provided in any appropriate manner. For example, in one embodiment, different compliances of the first and second restraining elements may be used to provide the different first and second restraining forces. More specifically, the second restraining elements may be less compliant than the first restraining elements. In another embodiment, the different first and second restraining forces may be provided using different numbers of the first and second restraining elements. In such an embodiment, a greater number of the second restraining elements may be used as compared to the number of first restraining elements. While specific methods of providing the different restraining forces have been noted above, other ways of providing the restraining forces are also contemplated.

In one possible embodiment, and as depicted in FIGS. 9-12, the first and second restraining elements 202 and 204 may correspond to tabs that extend inwards and distally relative to the inner tubular member 200 of the elongated shaft assembly. To provide the desired first and second restraining forces, a single more compliant first restraining element 202 and two less compliant second restraining elements 204 are incorporated into the rigid straight portion 12 of the inner tubular member 200 of the elongated shaft assembly. The tabs corresponding to the second restraining elements 204 may have reduced lengths and/or increased widths as compared to the tab corresponding to the first restraining element 202. Without wishing to be bound by theory, this results in the second restraining elements 204 being less compliant than the first restraining element 202. Consequently, due to the use of two less compliant tabs for the second restraining elements 204 as compared to a single more compliant tab for the first restraining element 202, the depicted embodiment is adapted to provide a second restraining force that is greater than the first restraining force. It should be understood that while a particular arrangement of first and second restraining elements has been depicted in the figures and described above, other embodiments for providing the first and second restraining forces are also possible.

Figure 13A:
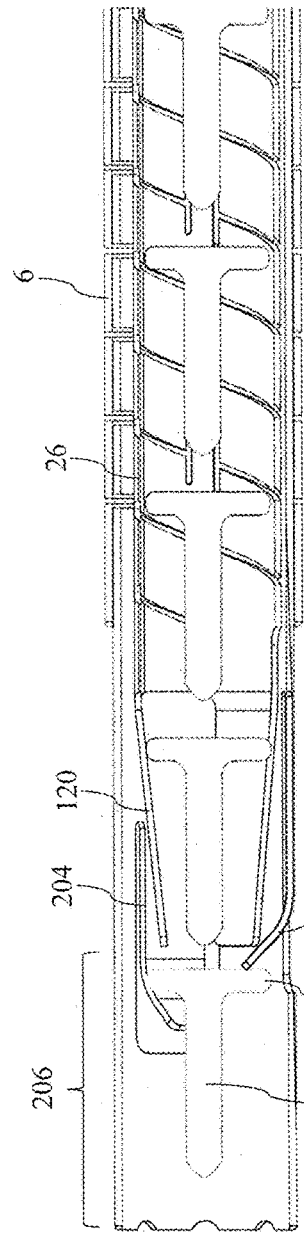
FIG. 13A is a cross-sectional view of the elongated shaft assembly, reciprocating driveshaft, and fasteners in the unactuated position.
Figure 13B:
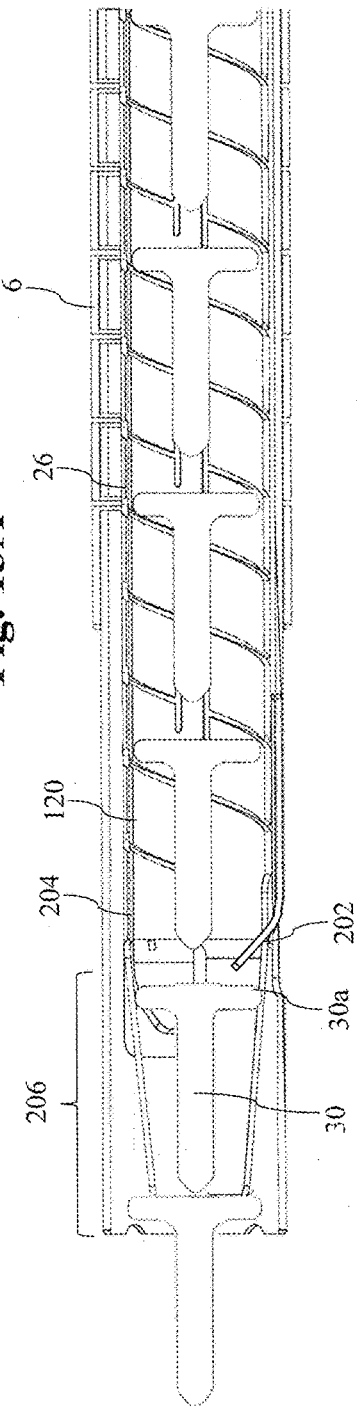
FIG. 13B is a cross-sectional view of the elongated shaft assembly, reciprocating driveshaft, and fasteners depicted in FIG. 13A in the actuated position.
Figure 13C:
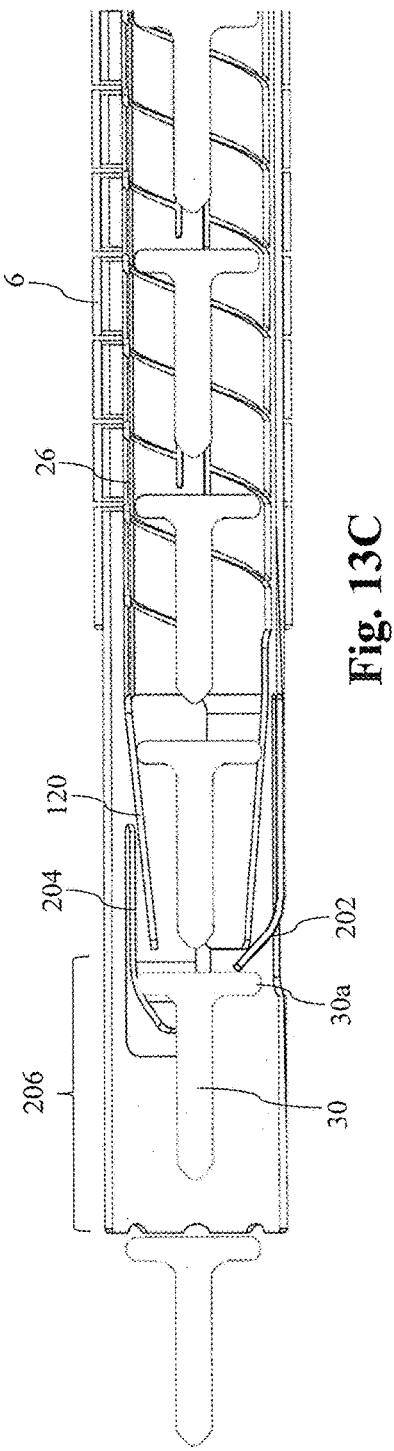
FIG. 13C is a cross-sectional view of the elongated shaft assembly, reciprocating driveshaft, and fasteners depicted in FIG. 13A after actuation.

The interaction between the first restraining elements 202, the second restraining elements 204, the fasteners 30, and the driveshaft 26 of the fastener deployment system are illustrated by FIGS. 13A- 13C depicting a series of cross-sections of a distal portion of the elongated shaft assembly 6 during actuation of the fastener deployment system. Prior to actuation, a distally located fastener 30 is positioned in the fastener deployment position 206. The fastener deployment position 206 may be defined by the relative locations of the first restraining elements 202 and the second restraining elements 204. The first restraining elements 202 and the second restraining elements 204 may define the fastener deployment position by retaining the head 30a of a fastener 30 between them prior to actuation. Retaining a fastener 30 in the fastener deployment position 206 using the restraining elements 202 and 204 may beneficially prevent a fastener from inadvertently being displaced out of the elongated shaft assembly 6 as well as providing a consistent position of a fastener for subsequent deployment. Upon actuation of the fastener deployment system, the driveshaft 26 is distally displaced resulting in the fastener driving elements 120 applying a force to the fastener 30 located in the fastener deployment position 206. The applied actuation force is greater than the second restraining force provided by the second restraining elements 204 resulting in the distal displacement and deployment of the fastener as depicted in FIG. 13B. As noted above, the stack of fasteners may have a separate force applied to distally displace the stack of fasteners and position the next fastener in the fastener deployment position 206 for the next actuation cycle. As the driveshaft 26 is withdrawn in a proximal direction to reset the fastener deployment system for the next actuation cycle, the fastener driving elements 120 deform around and past the head 30a of the fastener 30 located in the fastener deployment position 206, see FIG. 13C. As depicted in the figure, the tabs corresponding to the first and second restraining elements 202 and 204 may be arranged and adapted to resist proximal movement of a fastener 30 located distally from the restraining elements 202 and 204. Consequently, proximal movement of a fastener 30 located in the fastener deployment position 206 may be prevented by the first restraining element 202 as the driveshaft is moved in the proximal direction. Once the driveshaft 26 has been fully moved in the proximal direction, the surgical instrument is ready to deploy the next fastener.

While the above described embodiments have been directed to a follower that is driven by the reciprocating action of a driveshaft in a proximal and distal direction, other embodiments are possible. For example, in one embodiment, the follower might be associated with a rotating driveshaft such that rotation of the driveshaft may result in a distal displacement of the follower and the associated fasteners disposed within the driveshaft. In another exemplary embodiment, the follower might be associated with another component of the fastener deployment system such that actuation of the fastener deployment system results in a distal movement of the follower. For example, the follower might be associated with the trigger 14, the rigid linkage 20, or the shuttle 22. Further, the follower may be directly, or indirectly, associated with any of the above components.

Figure 14:
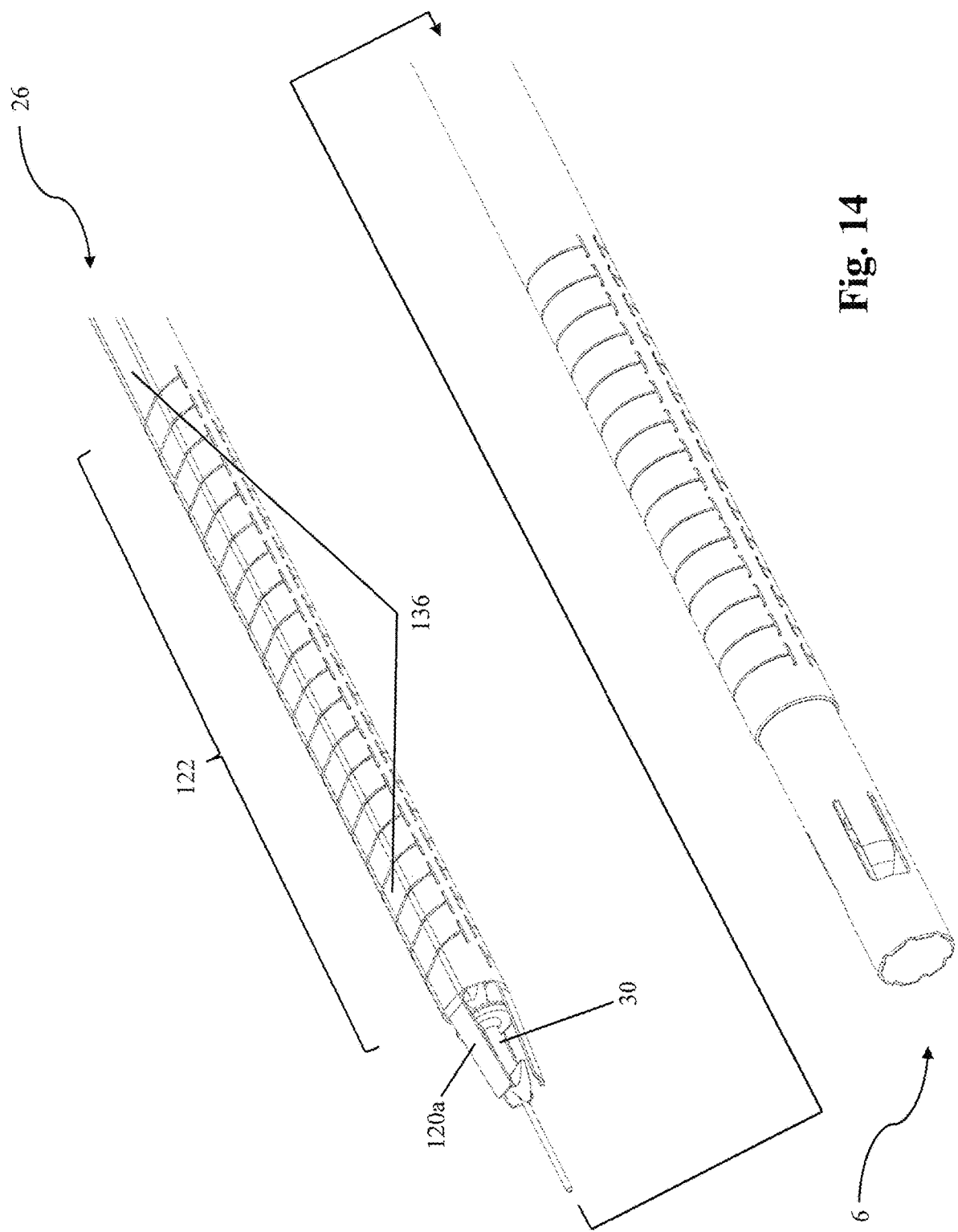
FIG. 14 is a schematic exploded view of the elongated shaft assembly and the reciprocating driveshaft including a stack of fasteners.

As noted previously, in addition to displacing the stack of fasteners to position the next fastener in the fastener deployment position, in some embodiments, it may be desirable to maintain a particular orientation of the fasteners within the elongated shaft assembly. FIG. 14 depicts a schematic exploded view of the elongated shaft assembly 6 and the driveshaft 26 which may be disposed within the interior of the elongated shaft assembly 6. The depicted pattern of slots formed in the exterior of the elongated shaft assembly 6 impart flexibility to the portion of the elongated shaft assembly 6 corresponding to the articulable portion 8. In the depicted embodiment, the driveshaft includes an internal channel to accommodate one or more fasteners 30 disposed therein. The driveshaft 26 may also include a guide surface 136. The guide surface 136 may be any appropriate shape, and as depicted in the figure, may correspond to a flat extending along the axial direction of the driveshaft 26. The guide surface 136 may interact with a corresponding surface on the fasteners 30 to maintain an orientation of the fasteners while they are disposed within the driveshaft 26 and as the driveshaft reciprocates between a distal position and a proximal position during actuation. In addition to the guide surface 136, the driveshaft 26 may also include a fastener driving element 120a that interacts with the corresponding surface on the fasteners 30 to maintain the orientation of a fastener 30 as it is positioned in the fastener deployment position.

In the depicted embodiment, a flat corresponding to the guide surface 136 is present on an internal surface of the internal channel of the driveshaft 26. Additionally, the guide surface 136 may optionally be present on an exterior surface of the driveshaft 26 as well. While a particular shape has been depicted for the guide surface 136, any appropriate shape or combination of features could be present on the driveshaft 26 to maintain an orientation of the fasteners 30 disposed therein. For example, the guide surface 136 may correspond to a protrusion, a groove, or any other appropriate shape. Further, the guide surface 136 may extend along any appropriate portion of the driveshaft 26. For example, the guide surface 136 might extend along a distal portion of the driveshaft, a flexible portion 122 of the driveshaft, a portion of the driveshaft corresponding to the stack of fasteners located within the driveshaft, or the entire length of the driveshaft as the current disclosure is not limited in this fashion.

FIGS. 15-17 depict one possible embodiment of a fastener 30 for use with the driveshaft 26. The depicted embodiment of the fastener 30 includes: a head 30a; a shaft 30b extending from the head 30a; and a barbed end 30c located at a distal end of the shaft 30b. A surface 138 corresponding to the guide surface 136 of the driveshaft may be disposed on the head 30a. The surface 138 may be sized and shaped to complement the guide surface 136 the driveshaft such that the fastener 30 smoothly interfaces with the internal surfaces of the driveshaft 26. In the depicted embodiment, the surface 138 corresponds to a flat such that a cross-section of the head 30a includes a flat portion and a round portion sized and shaped to complement corresponding flat and round portions of a cross-section of the internal channel of the driveshaft. While the surface 138 corresponding to the guide surface 136 has been depicted as being located on the head 30a of the fastener, the surface 138 might be located on any appropriate portion of the fastener 30. For example, a portion of the shaft 30b or barbed end 30c could include a corresponding surface, or feature, that is shaped, sized, and arranged to interact with the guide surface 136 of the driveshaft to maintain an orientation of the fastener 30.

In addition to the surface 138 present on the fastener 30 which corresponds to the guide surface 136, the fastener 30 may also include a through hole 140 extending distally from a proximal surface of the head 30a through the shaft 30b and the barbed end 30c. The through hole 140 may be sized and shaped to accommodate the fastener guide, as described above, to maintain the alignment of the fasteners 30 within the elongated shaft assembly. The through hole 140 may be centrally located, radially offset, or arranged in any other appropriate location as the current disclosure is not limited as to where the through hole 140 is located. While it may be desirable to include a through hole 140 to help maintain the alignment of the fasteners 30 within the elongated shaft assembly, it may also be desirable in certain embodiments to provide a pointed tip 142 on the fastener as depicted in the figure. However, embodiments using a blunt tip and an associated piercing needle are also envisioned. To accommodate the through hole 140, the pointed tip 142 may be radially offset relative to the through hole 140.

Figure 18:
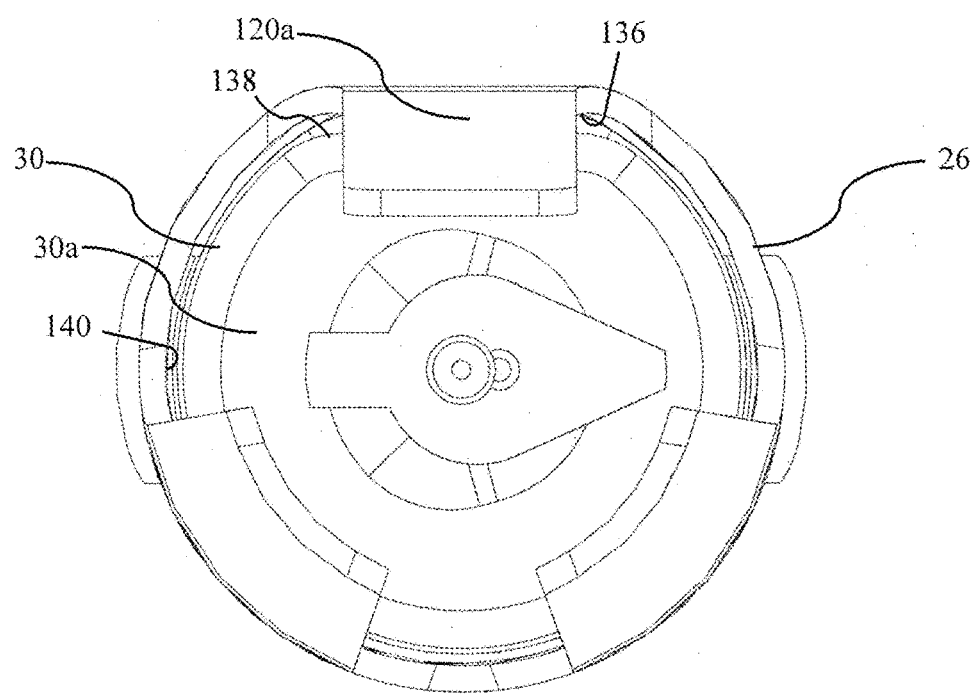
FIG. 18 is a schematic end view of the reciprocating driveshaft including a stack of fasteners disposed therein.

FIG. 18 depicts a distally located fastener 30 disposed within the internal channel 140 of the driveshaft 26. As illustrated by the figure, guide surface 136 and the fastener driving element 120a of the driveshaft 26 are aligned with the corresponding surface 138 of the fastener 30. Due to the interaction of the flat portions of the internal channel cross-section and the fastener head (i.e. the guide surface 136 and corresponding surface 138), as well as the round portions of the internal channel cross-section and the fastener head, the fastener 30 may be maintained in a preselected orientation throughout the length of the driveshaft 26.

Figure 19:
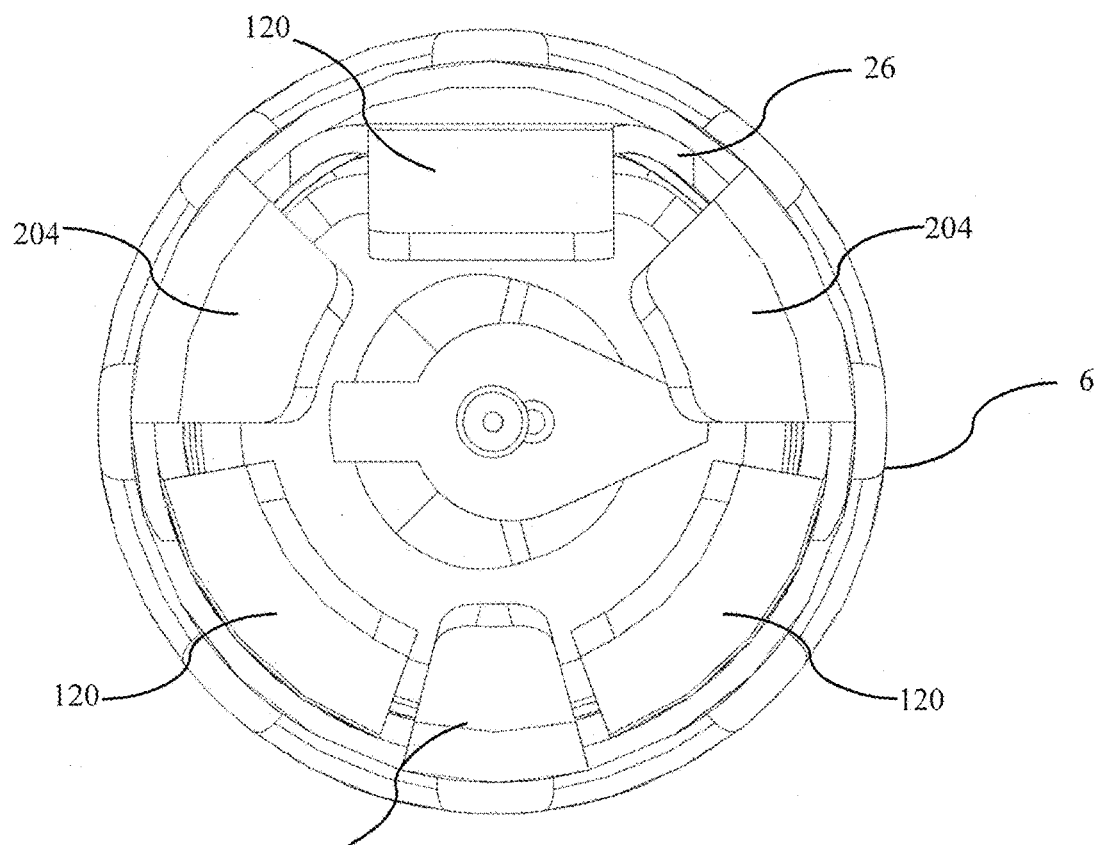
FIG. 19 is a schematic end view of the elongated shaft assembly with the reciprocating driveshaft and stack of fasteners disposed therein.

FIG. 19 depicts the fastener 30 and driveshaft 26 of FIG. 18 disposed within the elongated shaft assembly 6. As best illustrated by FIG. 13B, in some embodiments, the fastener driving elements 120 may extend distally relative to the first and second restraining elements 202 and 204 when the driveshaft 26 is distally displaced to deploy a fastener. Consequently, it may be desirable to arrange the fastener driving elements 120 and the first and second restraining elements 202 and 204 such that they do not interfere with one another during distal displacement of the driveshaft. In the depicted embodiment, the fastener driving elements 120 are arranged in a triangular pattern at a distal end of the driveshaft 26 and the first and second restraining elements 202 and 204 are arranged in another corresponding triangular pattern around the internal surface of the elongated shaft assembly 6 such that the fastener driving elements 122 do not interfere with the first and second restraining elements 202 and 204 during the distal displacement of the driveshaft. It should be understood that while a particular number and arrangement of the fastener driving elements and restraining elements has been depicted in the figures and described herein, the current disclosure is not limited in this manner. Instead, any appropriate number and arrangement of fastener driving elements and restraining elements might be used. Further, other appropriate types of fastener driving elements and restraining elements might also be used.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical instrument comprising:
a handle;
an elongated shaft extending distally from the handle, wherein the elongated shaft includes an articulable portion;
a distal most fastener disposed in the elongated shaft;
one or more fasteners disposed in the elongated shaft and located proximally to the distal most fastener;
a fastener deployment system configured to deploy the distal most fastener from the elongated shaft; and
a follower disposed within the elongated shaft, wherein actuation of the fastener deployment system to deploy the distal most fastener displaces the follower in a distal direction to displace the one or more fasteners in the distal direction, wherein the follower and the one or more fasteners are displaceable through the articulable portion of the elongated shaft while the articulable portion of the elongated shaft is articulated, wherein the follower is configured to conform to a shape of the articulate portion when the articulable portion is articulated.

2. The surgical instrument of claim 1, wherein the fastener deployment system includes a driveshaft disposed within the elongated shaft, wherein the follower and the one or more fasteners are disposed in an internal channel of the driveshaft.

3. The surgical instrument of claim 2, wherein distal displacement of the driveshaft deploys a distal most fastener from the elongated shaft, wherein distal displacement of the driveshaft displaces the follower in the distal direction.

4. The surgical instrument of claim 3, wherein the follower remains stationary when the driveshaft is proximally displaced.

5. The surgical instrument of claim 2, wherein the driveshaft includes a flexible portion configured to conform to a shape of the articulable portion.

6. The surgical instrument of claim 5, wherein the flexible portion is formed by a plurality of slots in the driveshaft.

7. The surgical instrument of claim 6, wherein the driveshaft includes at least one guide surface configured to maintain a rotational orientation of at least one fastener in the channel of the driveshaft, and wherein the at least one guide surface extends along the flexible portion.

8. The surgical instrument of claim 2, wherein the elongated shaft includes an articulable portion, and wherein the driveshaft includes a flexible portion configured to conform to a shape of the articulable portion.

9. The surgical instrument of claim 8, wherein the flexible portion is formed by a plurality of slots in the driveshaft.

10. The surgical instrument of claim 9, wherein the driveshaft includes at least one guide surface configured to maintain a rotational orientation of at least one fastener in the channel of the driveshaft, and wherein the at least one guide surface extends along the flexible portion.

11. The surgical instrument of claim 1, wherein during each actuation cycle the follower is compressed from a first length to a second length to apply a distally directed force to the one or more fasteners and displace the fasteners in the distal direction, and wherein during displacement of the one or more fasteners the follower expands from the second length to the first length.

12. The surgical instrument of claim 2, wherein the follower includes one or more tabs configured to engage with a plurality of openings extending along at least a portion of a length of the driveshaft to form a walking beam assembly.

13. A surgical instrument comprising:
a handle;
an elongated shaft extending distally from the handle;
a distal most fastener disposed in the elongated shaft;
one or more fasteners disposed in the elongated shaft and located proximally to the distal most fastener;
a driveshaft including a plurality of openings extending along at least a portion of a length of the driveshaft, wherein the driveshaft is configured to deploy the distal most fastener from the elongated shaft; and
a follower disposed within the elongated shaft, wherein the follower includes one or more tabs configured to engage with the plurality of openings to prevent proximal movement of the follower relative to the driveshaft while permitting distal movement of the follower, and wherein the follower is configured to displace the one or more fasteners in a distal direction when the driveshaft is actuated.

14. The surgical instrument of claim 13, further comprising an anti-backup mechanism configured to prevent proximal movement of the follower relative to the elongated shaft.

15. The surgical instrument of claim 13, wherein the follower remains stationary when the driveshaft is proximally displaced.

16. The surgical instrument of claim 15, wherein actuation of the driveshaft sequentially displaces the follower in the distal direction during each actuation cycle of the driveshaft.

17. The surgical instrument of claim 13, wherein the follower includes a driven element including the one or more tabs, a pushing element configured to contact the one or more fasteners, and an elastic element disposed between the driven element and the pushing element.

18. The surgical instrument of claim 13, wherein actuation of the driveshaft compresses the follower from a first length to a second length to apply a distally directed force to the one or more fasteners and displace the fasteners in the distal direction, and wherein during displacement of the one or more fasteners the follower expands from the second length to the first length.

19. The surgical instrument of claim 13, wherein each of the plurality of openings are spaced apart by approximately a single fastener length, and wherein the follower is displaced by approximately a single fastener length during each actuation cycle of the driveshaft.

* * * * *

UNITED STATES PATENT AND TRADEMARK OFFICE
CERTIFICATE OF CORRECTION

PATENT NO. : 11,234,693 B2  
APPLICATION NO. : 16/268596  
DATED : February 1, 2022  
INVENTOR(S) : Kevin J. Ranucci et al.

Page 1 of 1

It is certified that error appears in the above-identified patent and that said Letters Patent is hereby corrected as shown below:

In the Claims

At Column 18, Line 24, Claim 1, please delete "articulate" and substitute -- articulable --

Signed and Sealed this  
Twelfth Day of April, 2022

Drew Hirshfeld  
*Performing the Functions and Duties of the*  
*Under Secretary of Commerce for Intellectual Property and*  
*Director of the United States Patent and Trademark Office*